US012776030B2

(12) United States Patent
Tsujimoto

(10) Patent No.: US 12,776,030 B2
(45) Date of Patent: Oct. 27, 2026

(54) LEARNING APPARATUS, LEARNING METHOD, IMAGE PROCESSING APPARATUS, ENDOSCOPE SYSTEM, AND PROGRAM

(71) Applicant: FUJIFILM Corporation, Tokyo (JP)

(72) Inventor: Takayuki Tsujimoto, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 691 days.

(21) Appl. No.: 18/179,324

(22) Filed: Mar. 6, 2023

(65) Prior Publication Data

US 2023/0215003 A1 Jul. 6, 2023

Related U.S. Application Data

(63) Continuation of application No. PCT/JP2021/026537, filed on Jul. 15, 2021.

(30) Foreign Application Priority Data

Sep. 7, 2020 (JP) ................................ 2020-149586
Jun. 29, 2021 (JP) ................................ 2021-107406

(51) Int. Cl.
*G06T 7/00* (2017.01)
*A61B 1/00* (2006.01)
(Continued)

(52) U.S. Cl.
CPC ...... *G06T 7/0012* (2013.01); *A61B 1/000096* (2022.02); *G06N 3/0455* (2023.01);
(Continued)

(58) Field of Classification Search
CPC .................... G06T 7/0012; G06T 7/11; G06T 2207/10068; G06T 2207/20081;
(Continued)

(56) References Cited

U.S. PATENT DOCUMENTS

2019/0117167 A1* 4/2019 Kamiyama .............. A61B 1/04
2019/0164287 A1* 5/2019 Gregson ................ G06V 10/82
(Continued)

FOREIGN PATENT DOCUMENTS

JP 2012026982 2/2012
JP 2020030565 2/2020
(Continued)

OTHER PUBLICATIONS

"International Search Report (Form PCT/ISA/210) of PCT/JP2021/026537", mailed on Oct. 19, 2021, with English translation thereof, pp. 1-5.
(Continued)

*Primary Examiner* — Van D Huynh
(74) *Attorney, Agent, or Firm* — JCIPRNET

(57) ABSTRACT

There are provided a learning apparatus, a learning method, an image processing apparatus, an endoscope system, and a program that enable generation of training data on the basis of output data from a learning model for which learning is performed by using normality data. A first learning model (500) is generated by performing first learning using normality data (502) as learning data or by performing first learning using as learning data, normality mask data (504) that is generated by making a part of normality data be lost, and second training data to be applied to a second learning model that identifies identification target data is generated
(Continued)

by using output data output from the first learning model in response to input of abnormality data to the first learning model.

19 Claims, 12 Drawing Sheets

(51) Int. Cl.
*G06N 3/0455* (2023.01)
*G06T 7/11* (2017.01)

(52) U.S. Cl.
CPC ...... *G06T 7/11* (2017.01); *G06T 2207/10068* (2013.01); *G06T 2207/20081* (2013.01); *G06T 2207/20084* (2013.01); *G06T 2207/30096* (2013.01)

(58) Field of Classification Search
CPC . G06T 2207/20084; G06T 2207/30096; G06T 2207/30032; G06T 7/00; A61B 1/000096; A61B 1/000094; G06N 3/0455; G06N 3/0895; G06N 3/09; G06N 3/0464; G06N 3/045; G06N 3/047; G06N 3/0475; G06N 3/094
See application file for complete search history.

(56) References Cited

U.S. PATENT DOCUMENTS

| | | | | |
|---|---|---|---|---|
| 2020/0074622 | A1 * | 3/2020 | Yang | A61B 3/102 |
| 2020/0226752 | A1 * | 7/2020 | Lee | G06T 7/0012 |
| 2020/0349470 | A1 * | 11/2020 | Ikeda | G06F 18/214 |
| 2021/0161363 | A1 * | 6/2021 | Makino | G06N 3/08 |
| 2022/0180495 | A1 * | 6/2022 | Higa | G06T 7/0002 |
| 2022/0414870 | A1 * | 12/2022 | Rexhepaj | G06T 7/0012 |
| 2023/0005251 | A1 * | 1/2023 | Take | G06N 3/094 |

FOREIGN PATENT DOCUMENTS

| | | |
|---|---|---|
| JP | 2020032190 | 3/2020 |
| WO | 2019159853 | 8/2019 |

OTHER PUBLICATIONS

"Written Opinion of the International Searching Authority (Form PCT/ISA/237) of PCT/JP2021/026537", mailed on Oct. 19, 2021, with English translation thereof, pp. 1-6.

* cited by examiner

LEARNING APPARATUS, LEARNING METHOD, IMAGE PROCESSING APPARATUS, ENDOSCOPE SYSTEM, AND PROGRAM

CROSS-REFERENCE TO RELATED APPLICATIONS

The present application is a Continuation of PCT International Application No. PCT/JP2021/026537 filed on Jul. 15, 2021 claiming priorities under 35 U.S.C § 119(a) to Japanese Patent Application No. 2020-149586 filed on Sep. 7, 2020 and Japanese Patent Application No. 2021-107406 filed on Jun. 29, 2021. Each of the above applications is hereby expressly incorporated by reference, in its entirety, into the present application.

BACKGROUND OF THE INVENTION

1. Field of the Invention

The present invention relates to a learning apparatus, a learning method, an image processing apparatus, an endoscope system, and a program.

2. Description of the Related Art

To identify an abnormal region, such as a lesion, from an image, a method of training AI (Artificial Intelligence) by using a large number of images and pieces of training data corresponding to the respective images is known. Examples of the training data include an image in which an abnormal region is labeled 1 and a normal region is labeled 0. AI performs learning with the image and the labels as learning data.

Examples of the learning include deep learning. As a technique of deep learning, distillation is known. Distillation is a technique of learning in which an output from trained AI for an image is given to AI that is to be trained as training data. Examples of the output from trained AI include a probability distribution that indicates a class to which the input image belongs.

AI that is to be trained is lighter than trained AI and smaller in size as a learning model but is able to perform identification with accuracy comparable with that of trained AI. Examples of an output from trained AI include a set of an abnormality probability and a normality probability. Examples of the set of an abnormality probability and a normality probability include (abnormality probability, normality probability)=(1, 0) and (abnormality probability, normality probability)=(0.8, 0.2).

JP2020-30565A describes an image determination method using machine learning. In the image determination method described in JP2020-30565A, a normality model generated by performing learning with only normality images as a learning data set is applied, the degree of deviation that is an error between an output value output in response to input of a determination target image to the normality model and a normal state of the determination target image is calculated on a pixel-by-pixel basis, and the determination target image is determined to be an abnormality image when the sum of the degrees of deviation is large.

JP2012-26982A describes a test apparatus that determines the presence or absence of an abnormality in a test target signal. The apparatus described in JP2012-26982A applies a first processing unit including a first neural network for which learning for classifying types of abnormalities is performed by using only normal test target signals to classify a test target signal as a normal signal or a signal other than a normal signal.

SUMMARY OF THE INVENTION

To prepare trained AI, a large amount of abnormality data and a large amount of normality data are necessary. Acquisition of normality data is easier than that of abnormality data while abnormality data is rare and acquisition of a large amount of abnormality data is difficult. In the medical field, the number of abnormality images significantly differs from case to case. Therefore, preparation of trained AI is difficult because of difficulty of acquiring a large amount of abnormality data.

The above-described issue is not limited to identification of an abnormal region in a medical image, and a similar issue is also present in recognition of a feature region in a usual image, to which a trained learning model is applied. The above-described issue is not limited to images, and a similar issue is also present in identification of abnormality data in usual signal processing, to which a trained learning model is applied.

In the invention described in JP2020-30565A, a learning model trained by using only normality images is included and this learning model outputs the degree of deviation that is an error from a normal state of a determination target image, and therefore, to determine whether the determination target image is a normality image, a processing unit that evaluates the degree of deviation and a processing unit that performs determination based on the evaluation of the degree of deviation are necessary in addition to the learning model.

In the invention described in JP2012-26982A, a learning model trained by using captured images of normal test target objects is applied, and the presence or absence of a defect in a test target object relative to the normal test target objects is output, and therefore, to determine whether the test target object is normal, a processing unit that evaluates a defect in the test target object and a processing unit that determines whether the test target object is normal on the basis of the result of evaluation are necessary in addition to the learning model.

The present invention has been made in view of the above-described circumstances, and an object thereof is to provide a learning apparatus, a learning method, an image processing apparatus, an endoscope system, and a program that enable generation of training data on the basis of output data from a learning model for which learning is performed by using normality data.

To achieve the above-described object, the following aspects of the invention are provided.

A learning apparatus according to the present disclosure is a learning apparatus including at least one processor, the processor being configured to generate a first learning model by performing first learning using normality data as learning data or by performing first learning using as learning data, normality mask data that is generated by making a part of normality data be lost, and generate second training data to be applied to a second learning model that identifies identification target data, by using output data output from the first learning model in response to input of abnormality data to the first learning model.

With the learning apparatus according to the present disclosure, the second training data to be applied to learning for the second learning model is generated on the basis of the output data output from the first learning model in response to input of the abnormality data to the first learning model for which learning is performed by using the normality data. Accordingly, the second learning model can be generated by performing second learning based on the second training data.

To the input data, an image captured by using an image capturing device can be applied.

To the second training data, a probability distribution that indicates a class to which the input data belongs can be applied.

In the learning apparatus according to another aspect, the processor is configured to generate the first learning model that outputs, for input data having a lost part, output data in which the lost part is compensated for.

According to the above-described aspect, the first learning model that generates restoration data corresponding to the input data can be generated.

In the learning apparatus according to another aspect, the processor is configured to generate the first learning model that reduces a dimension of input data and outputs output data for which the reduced dimension is restored.

According to the above-described aspect, first learning model that performs an efficient process at a high speed with a reduced processing load can be generated.

In the learning apparatus according to another aspect, the processor is configured to generate the first learning model that outputs output data having a size the same as a size of input data.

According to the above-described aspect, a processing load when the output data from the first learning model is processed can be reduced.

In the learning apparatus according to another aspect, the processor is configured to generate the first learning model to which a generative adversarial network is applied, by performing the first learning using the normality mask data as learning data.

According to the above-described aspect, the first learning model can be generated by performing unsupervised learning using the normality mask data.

In the learning apparatus according to another aspect, the processor is configured to generate the first learning model to which an autoencoder is applied, by performing the first learning using the normality data as learning data.

According to the above-described aspect, the first learning model for which unsupervised learning is performed by using the normality data can be generated.

In the learning apparatus according to another aspect, the processor is configured to generate the second training data by using a difference between input data and output data for the first learning model.

According to the above-described aspect, the second training data to be applied to the second learning model can be generated by using the output data from the first learning model for which learning is performed by using the normality data.

In the learning apparatus according to another aspect, the processor is configured to generate abnormality mask data that is generated by making an abnormal part of the abnormality data be lost, and generate the second training data by normalizing difference data that is a difference between the abnormality data input to the first learning model and output data output in response to input of the abnormality mask data to the first learning model.

According to the above-described aspect, the second training data in a form that is easily handled in the second learning to be applied to the second learning model can be generated.

In the learning apparatus according to another aspect, the processor is configured to generate the second learning model by performing second learning using a set of abnormality data and the second training data as learning data.

According to the above-described aspect, the second learning that is applied to the second learning model and that uses the abnormality data and the second training data corresponding to the abnormality data can be performed.

In the learning apparatus according to another aspect, the processor is configured to perform the second learning using a set of the normality data and first training data corresponding to the normality data as learning data.

According to the above-described aspect, the second learning that is applied to the second learning model and that uses the normality data and the first training data corresponding to the normality data can be performed.

In the learning apparatus according to another aspect, the processor is configured to perform second learning for the second learning model by using as the second training data, a hard label that has discrete training values indicating the normality data and the abnormality data and that is applied to the first learning and a soft label that has continuous training values indicating an abnormality-likeness and that is generated by using output data from the first learning model.

According to the above-described aspect, the hard label is used to classify definite normality data and definite abnormality data, and the soft label is used to classify normality data similar to abnormality data and abnormality data similar to normality data. Accordingly, the accuracy and efficiency of classification of normality data and abnormality data can be improved.

In the learning apparatus according to another aspect, the processor is configured to perform the second learning a plurality of times, and not increase a weight used for the hard label and not decrease a weight used for the soft label as the number of times the second learning is performed increases.

According to the above-described aspect, in a stage in which the number of times learning is performed is relatively small, classification of definite normality data and definite abnormality data takes precedence over others, and as the number of times learning is performed becomes relatively large, classification of normality data similar to abnormality data and abnormality data similar to normality data takes precedence over others. Accordingly, the accuracy and efficiency of classification of normality data and abnormality data can be improved.

In the learning apparatus according to another aspect, the processor is configured to generate the second learning model to which a convolutional neural network is applied.

According to the above-described aspect, the second learning model to which deep learning is applied can be generated.

A learning method according to the present disclosure is a learning method for causing a computer to generate a first learning model by performing first learning using normality data as learning data or by performing first learning using as learning data, normality mask data that is generated by making a part of normality data be lost, and generate second training data to be applied to a second learning model that identifies identification target data, by using output data output from the first learning model in response to input of abnormality data to the first learning model.

With the learning method according to the present disclosure, effects similar to those attained by the learning apparatus according to the present disclosure can be attained.

In the learning method according to the present disclosure, configurations similar to those of the learning apparatus according to other aspects of the present disclosure can be employed.

An image processing apparatus according to the present disclosure is an image processing apparatus including at least one processor, the processor being configured to generate a second learning model by performing second learning using a set of second training data and an abnormality image as learning data, the second training data being generated by using an output image output from a first learning model in response to input of an abnormality image to the first learning model, the second training data being applied to the second learning model that identifies presence or absence of an abnormality in an identification target image, the first learning model being generated by performing first learning using a normality image as learning data or by performing first learning using as learning data, a normality mask image that is generated by making a part of a normality image be lost, and determine whether an identification target image is a normality image by using the second learning model.

With the image processing apparatus according to the present disclosure, effects similar to those attained by the learning apparatus according to the present disclosure can be attained.

In the image processing apparatus according to the present disclosure, configurations similar to those of the learning apparatus according to other aspects of the present disclosure can be employed.

In the image processing apparatus according to another aspect, the second learning model performs segmentation of an abnormal part for the identification target image.

According to the above-described aspect, image identification to which segmentation is applied can be performed.

An endoscope system according to the present disclosure is an endoscope system including: an endoscope; and at least one processor, the processor being configured to generate a second learning model by performing second learning using a set of second training data and an abnormality image as learning data, the second training data being generated by using an output image output from a first learning model in response to input of an abnormality image to the first learning model, the second training data being applied to the second learning model that identifies presence or absence of an abnormality in an identification target image, the first learning model being generated by performing first learning using a normality image as learning data or by performing first learning using as learning data, a normality mask image that is generated by making a part of a normality image be lost, and determine presence or absence of an abnormality in an endoscopic image acquired from the endoscope, by using the second learning model.

With the endoscope system according to the present disclosure, effects similar to those attained by the learning apparatus according to the present disclosure can be attained.

In the endoscope system according to the present disclosure, configurations similar to those of the learning apparatus according to other aspects of the present disclosure can be employed.

In the endoscope system according to another aspect, the processor is configured to perform the second learning by applying the second training data that is generated by using the first learning model for which the first learning is performed by applying an endoscopic image that is a normal mucous membrane image as the normality image, and by applying an endoscopic image that includes a lesion region as the abnormality image.

According to the above-described aspect, highly accurate identification of a lesion for an endoscopic image can be performed by using the second learning model that has been trained.

In the endoscope system according to another aspect, the processor is configured to perform the second learning by using a set of the second training data and the abnormality image and a set of a normality image and first training data corresponding to the normality image as learning data, and generate the second learning model that performs segmentation of an abnormal part in an identification target image, the second training data corresponding to the abnormality image and generated by normalizing difference data that is a difference between the abnormality image and an output image output from the first learning model in response to input of an abnormality mask image that is generated by making an abnormal part of the abnormality image be lost to the first learning model, the first learning performed for the first learning model being learning for restoring the normal mucous membrane image from a normal mucous membrane mask image generated by making a part of the normal mucous membrane image be lost and for generating a normality restoration image.

According to the above-described aspect, highly accurate identification of a lesion based on segmentation of an abnormal part for an endoscopic image can be performed by using the second learning model that has been trained.

A program according to the present disclosure is a program for causing a computer to implement a function of generating a first learning model by performing first learning using normality data as learning data or by performing first learning using as learning data, normality mask data that is generated by making a part of normality data be lost, and a function of generating second training data to be applied to a second learning model that identifies presence or absence of an abnormality in identification target data, by using output data output from the first learning model in response to input of abnormality data to the first learning model.

With the program according to the present disclosure, effects similar to those attained by the learning apparatus according to the present disclosure can be attained.

In the program according to the present disclosure, configurations similar to those of the learning apparatus according to other aspects of the present disclosure can be employed.

A learning apparatus according to the present disclosure is a learning apparatus including at least one processor, the processor being configured to generate a first learning model by performing first learning using first training data to which a hard label having discrete training values indicating normality data and abnormality data is applied, generate a soft label having continuous training values indicating an abnormality-likeness by using output data output from the first learning model in response to input of abnormality data to the first learning model, and perform second learning that is applied to a second learning model that identifies identification target data, by using the hard label and the soft label as second training data.

With the learning apparatus according to the present disclosure, the second learning model for classifying definite normality data and definite abnormality data by using the hard label and for classifying normality data similar to abnormality data and abnormality data similar to normality data by using the soft label can be generated. Accordingly, the accuracy and efficiency of classification of normality data and abnormality data can be improved.

In the learning apparatus according to another aspect, the processor is configured to perform the first learning using as learning data, a set of the normality data and the first training data corresponding to the normality data and a set of the abnormality data and the first training data corresponding to the abnormality data as learning data applied to the first learning.

According to the above-described aspect, the first learning model can be generated by performing the first learning based on the normality data and the abnormality data.

In the learning apparatus according to another aspect, the processor is configured to perform the second learning a plurality of times, and not increase a weight used for the hard label and not decrease a weight used for the soft label as the number of times the second learning is performed increases.

According to the above-described aspect, when the number of times learning is performed is relatively small, classification of definite normality data and definite abnormality data takes precedence over others, and when the number of times learning is performed is relatively large, classification of normality data similar to abnormality data and abnormality data similar to normality data takes precedence over others. Accordingly, the accuracy and efficiency of classification of normality data and abnormality data can be improved.

A learning method according to the present disclosure is a learning method for causing a computer to generate a first learning model by performing first learning using first training data to which a hard label having discrete training values indicating normality data and abnormality data is applied, generate a soft label having continuous training values indicating an abnormality-likeness by using an output that is output from the first learning model in response to input of abnormality data to the first learning model, and perform second learning that is applied to a second learning model that identifies identification target data, by using the hard label and the soft label.

With the learning method according to the present disclosure, effects similar to those attained by the learning apparatus according to the present disclosure can be attained.

In the learning method according to the present disclosure, configurations similar to those of the learning apparatus according to other aspects of the present disclosure can be employed.

An image processing apparatus according to the present disclosure is an image processing apparatus including at least one processor, the processor being configured to generate a first learning model by performing first learning using first training data to which a hard label having discrete training values indicating a normality data and an abnormality data is applied, generate a soft label having continuous training values indicating an abnormality-likeness by using an output that is output from the first learning model in response to input of an abnormality image to the first learning model, generate a second learning model by performing second learning that is applied to the second learning model that identifies identification target data, by using the hard label and the soft label, and determine whether an identification target image is a normality image by using the second learning model.

With the image processing apparatus according to the present disclosure, effects similar to those attained by the learning apparatus according to the present disclosure can be attained.

In the image processing apparatus according to the present disclosure, configurations similar to those of the learning apparatus according to other aspects of the present disclosure can be employed.

An endoscope system according to the present disclosure is an endoscope system including: an endoscope; and at least one processor, the processor being configured to generate a first learning model by performing first learning using first training data to which a hard label having discrete training values indicating a normality pixel and an abnormality pixel is applied, generate a soft label having continuous training values indicating an abnormality-likeness by using an output that is output from the first learning model in response to input of an abnormality image to the first learning model, generate a second learning model by performing second learning that is applied to the second learning model that identifies identification target data, by using the hard label and the soft label, and determine whether an identification target image is a normality image by using the second learning model.

With the endoscope system according to the present disclosure, effects similar to those attained by the learning apparatus according to the present disclosure can be attained.

In the endoscope system according to the present disclosure, configurations similar to those of the learning apparatus according to other aspects of the present disclosure can be employed.

According to the present disclosure, the second training data to be applied to learning for the second learning model is generated on the basis of the output data output from the first learning model in response to input of the abnormality data to the first learning model for which learning is performed by using the normality data. Accordingly, the second learning model can be generated by performing the second learning based on the second training data, and therefore, an abnormal region, such as a lesion, can be identified from an image or determination as to whether a test target object is normal can be easily performed without a large amount of abnormality data.

DESCRIPTION OF THE PREFERRED EMBODIMENTS

Figure 1:
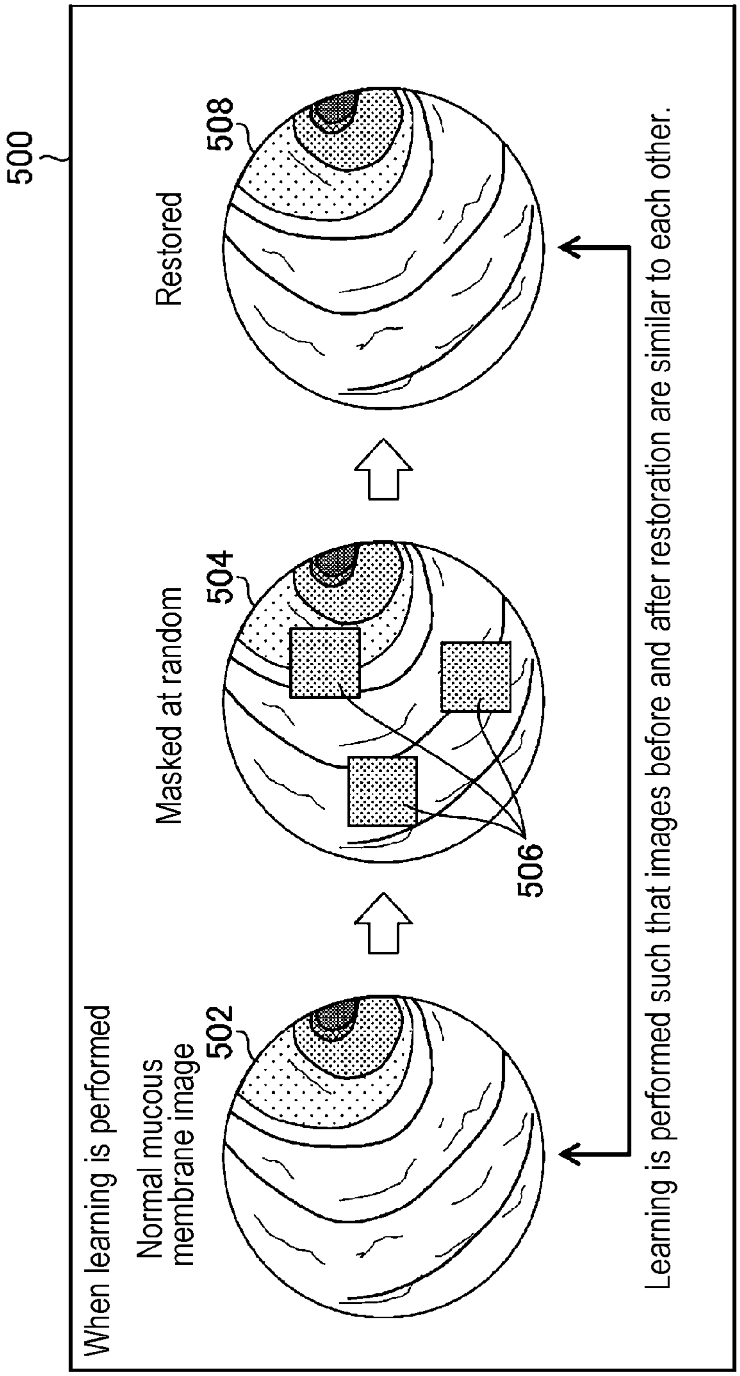
FIG. 1 is a schematic diagram of first learning applied to a first learning model.

Hereinafter, preferred embodiments of the present invention will be described in detail with reference to the attached drawings. In the specification, the same components are assigned the same reference numerals, and a duplicated description thereof is omitted as appropriate.

Example Configuration of Learning Apparatus According to First Embodiment

A learning apparatus according to a first embodiment is applied to an image processing apparatus that identifies a lesion region from an endoscopic image that is a moving image captured by using an endoscope. The learning apparatus is assigned a reference numeral 600 and illustrated in FIG. 6. Identification is a concept that includes detection of the presence or absence of a feature region in an identification target image. Identification may include identification of the type of a detected feature region.

Example of First Learning

FIG. 1 is a schematic diagram of first learning applied to a first learning model. A first learning model 500 that performs the first learning illustrated in FIG. 1 performs the first learning by using a normal mucous membrane image 502 that is acquired from a moving image captured by using an endoscope and that includes only a normal mucous membrane. In the first learning, a large number of normal mucous membrane images 502 are prepared. For example, about 2000 normal mucous membrane images 502 are prepared. Note that the term "learning model" is synonymous with, for example, "leaner".

Next, a random mask process for masking inner parts of the normal mucous membrane image 502 at random is performed to generate a normality mask image 504. The normality mask image 504 illustrated in FIG. 1 has mask regions 506 at three locations.

The mask regions 506 can have, for example, a rectangular shape, a round shape, or an elliptical shape. To the mask process for generating the mask regions 506, a free form using random numbers can be applied.

In the first learning, learning is performed in which the normality mask image 504 is input to a CNN that is applied to the first learning model, the mask regions 506 are restored, and a restoration image 508 is generated. In other words, the first learning model 500 performs learning for generating the restoration image 508 from the normal mucous membrane image 502. Note that CNN is an acronym for Convolutional Neural Network.

That is, the first learning is learning for making images before and after restoration be similar to each other. For example, in the first learning, information about pixels around the mask regions 506 in the normality mask image 504 is used to compensate for lost regions, that is, the mask regions 506 in the normal mucous membrane image 502.

Note that the normal mucous membrane image 502 described in the embodiment is an example of normality data and an example of a normality image. The normality mask image 504 described in the embodiment is an example of normality mask data and an example of a normal mucous membrane mask image. The restoration image 508 described in the embodiment is an example of a normality restoration image.

Figure 2:
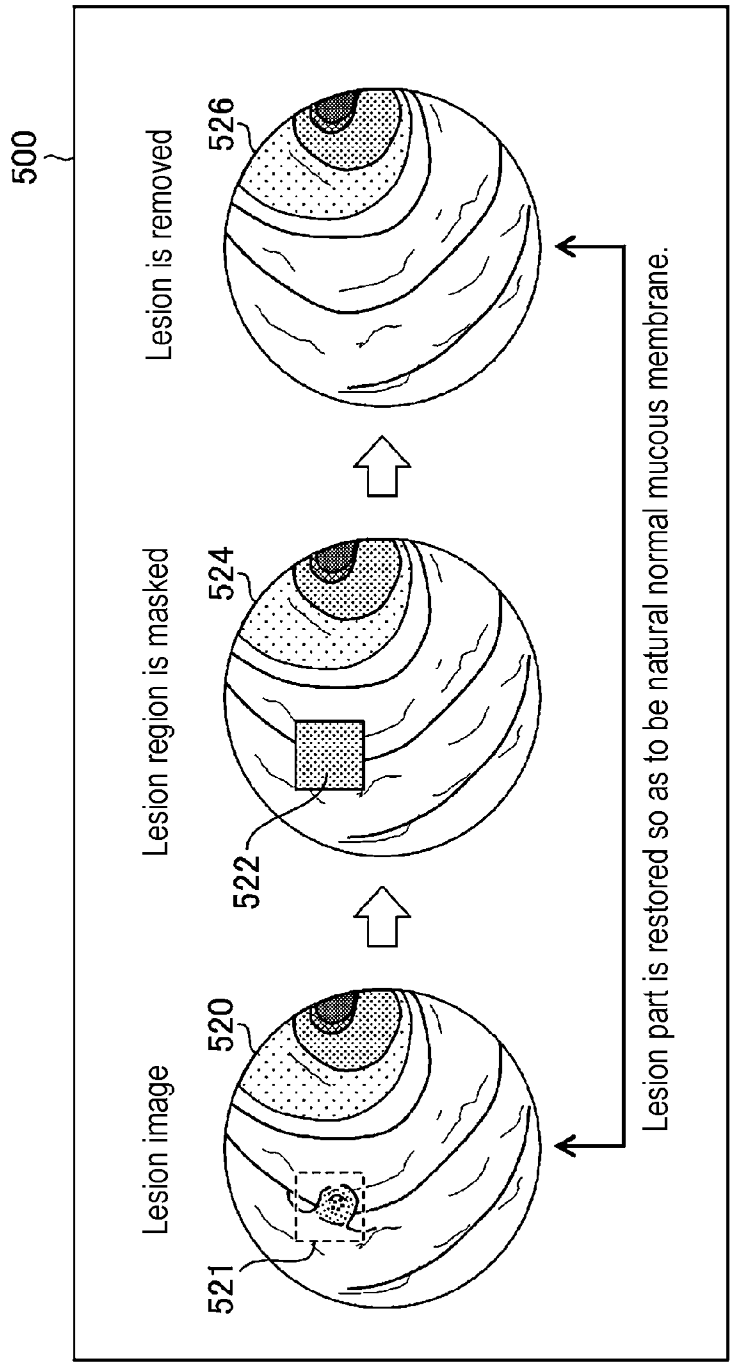
FIG. 2 is a schematic diagram of the first learning model that has been trained.

FIG. 2 is a schematic diagram of the first learning model that has been trained. The first learning model 500 that has been trained generates, for a lesion image 520 that is a frame image from an endoscopic image and that includes a lesion, a pseudo normal mucous membrane image 526 from an abnormality mask image 524 that includes a mask region 522 acquired by masking a lesion region 521. In the pseudo normal mucous membrane image 526, the lesion region 521 in the lesion image 520 is restored so as to be a natural normal mucous membrane.

The first learning model 500 has learned only the normal mucous membrane image 502 illustrated in FIG. 1 and has not learned an image, such as the lesion image 520, other than the normal mucous membrane image 502, and therefore, compensates for the mask region 522 that is originally the lesion region 521 by an image that looks like a normal mucous membrane and that is estimated from pixels of a region of a normal mucous membrane around the mask region 522.

Note that the lesion image 520 described in the embodiment is an example of abnormality data, an example of input data, and an example of an abnormality image. The pseudo normal mucous membrane image 526 described in the embodiment is an example of output data. The lesion region 521 described in the embodiment is an example of an abnormal part. The abnormality mask image 524 described in the embodiment is an example of abnormality mask data.

Figure 3:
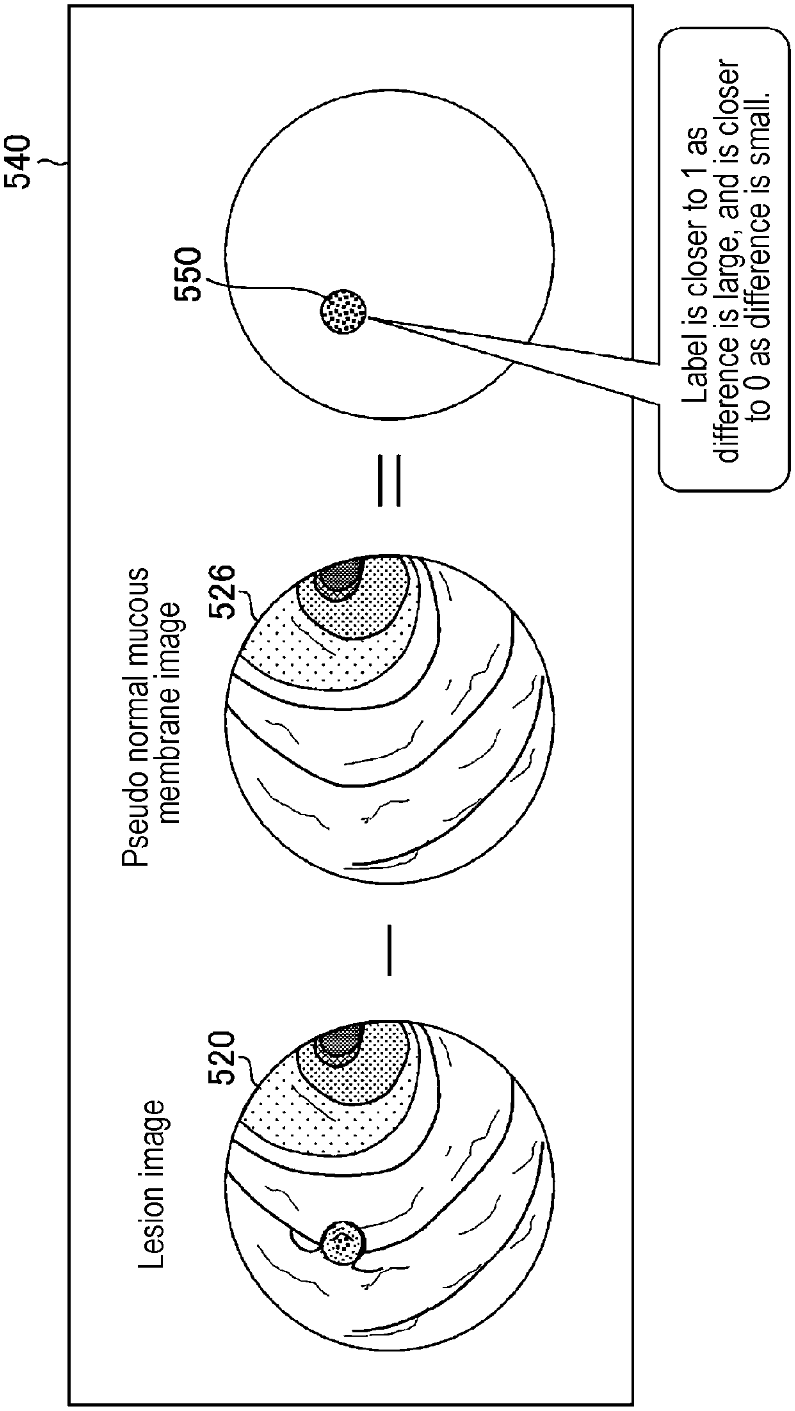
FIG. 3 is a schematic diagram of generation of second training data by using the first learning model.

FIG. 3 is a schematic diagram of generation of second training data by using the first learning model. A second training data generation unit 540 that generates second training data derives difference data 550 that is the difference between the lesion image 520 input to the first learning model 500 illustrated in FIG. 1 and the pseudo normal mucous membrane image 526 that is an output from the first learning model 500. FIG. 3 schematically illustrates the difference data 550.

The difference data 550 can be a set of subtraction values, for respective pixels, each of which is acquired by subtracting from the pixel value of each pixel of the lesion image 520, the pixel value of a pixel of the pseudo normal mucous membrane image 526 corresponding to the pixel of the lesion image 520.

The difference data 550 that is the difference between the lesion image 520 and the pseudo normal mucous membrane image 526 is relatively small when the lesion in the lesion image 520 is similar to a normal mucous membrane. In contrast, the difference data 550 that is the difference between the lesion image 520 and the pseudo normal mucous membrane image 526 is relatively large when the lesion in the lesion image 520 is dissimilar to a normal mucous membrane.

When the difference data can have any value within a range from −255 to 255, normalization may be performed in which the value within a range from −255 to 255 is normalized to, for example, a value within a range from 0 to 1, a value within a range from −1 to 1, or a value within a range from ½ to 1, and the resulting data may be used as the second training data corresponding to the lesion image 520.

When the second training data is assumed to have a value within a range from 0 to 1 and when the difference data 550 that is the difference between the lesion image 520 and the pseudo normal mucous membrane image 526 is relatively large, the second training data corresponding to the lesion image 520 is closer to 1. In contrast, when the difference data 550 that is the difference between the lesion image 520 and the pseudo normal mucous membrane image 526 is relatively small, the second training data corresponding to the lesion image 520 is closer to 0.

To the first learning model, a GAN is applied. GAN is an acronym for Generative Adversarial Network. The first learning model 500 in which a GAN is applied to the CNN has an advantage that the restoration image 508 becomes distinct.

The GAN includes a generator and a discriminator. The generator is trained so as to restore the normal mucous membrane image 502 from the normality mask image 504 illustrated in FIG. 1. The discriminator is trained so as to determine whether the restoration image 508 generated as a result of restoration is a restoration image of the normal mucous membrane image 502 that is input. The generator and the discriminator learn from each other, and the generator can finally generate the restoration image 508 close to the normal mucous membrane image 502. To the loss function, for example, the cross-entropy, the hinge loss, or the L2 loss can be applied.

In the first learning model 500, an input image and an output image have the same size. That is, in the first learning model 500, the output size and the input size are the same.

Example of Second Learning

Figure 4:
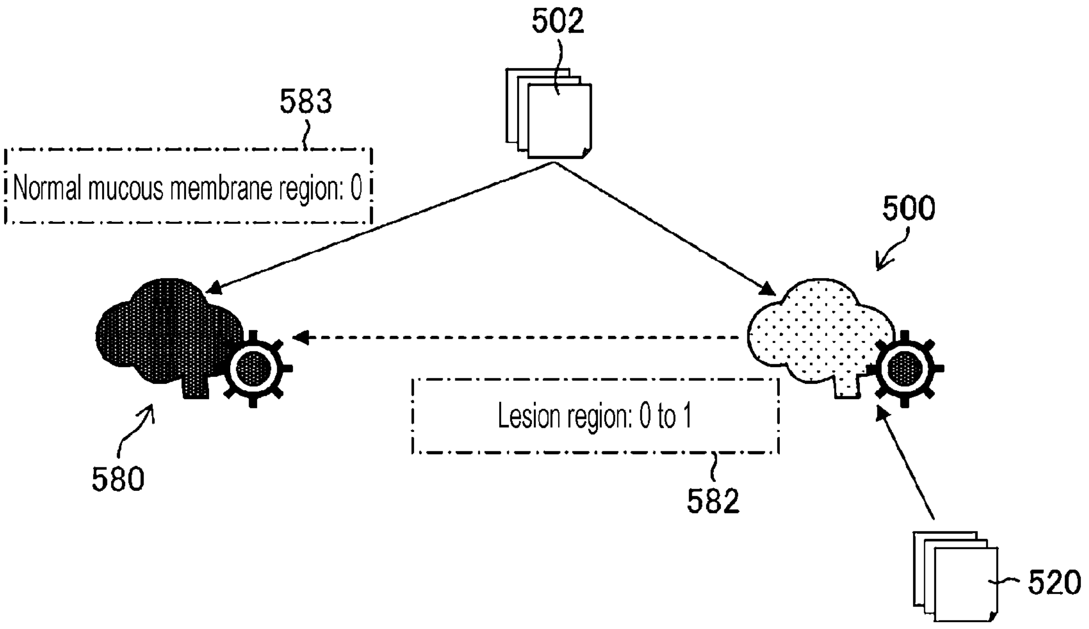
FIG. 4 is a conceptual diagram of second learning.

FIG. 4 is a conceptual diagram of second learning. For a second learning model 580 illustrated in FIG. 4, learning is performed by using second training data 582 generated on the basis of an output from the first learning model 500 that has been trained. The point of the learning apparatus described in the embodiment is that only the normal mucous membrane image 502 is used as a learning data set in the first learning in which the second training data 582 that is applied to the second learning for the second learning model 580 is generated.

To the second training data 582 applied to the second learning for the second learning model 580, a score that is normalized to any value within a range from 0 to 1 and that indicates a lesion-likeness is applied. The second training data 582 has a score closer to 0 as the lesion region is more similar to a normal mucous membrane. In contrast, the second training data 582 has a score closer to 1 as the lesion region is more dissimilar to a normal mucous membrane. To training data 583 corresponding to a normal mucous membrane region, a score of 0 indicating a normal mucous membrane region is applied. As the training data 583, first training data applied to learning for the first learning model may be used. Note that the score described here is synonymous with "training value".

That is, to the second learning, a set of the lesion image 520 and the second training data 582 corresponding to the lesion image 520 and a set of the normal mucous membrane image 502 and the training data 583 corresponding to the normal mucous membrane image 502 are applied as a learning data set.

For the second learning model 580, the second learning is performed as learning for the CNN for segmentation of an identification target image, by using the learning data set described above. Note that the identification target image described in the embodiment is an example of identification target data.

In the second learning that is learning for the CNN for segmentation, only the second training data 582 having any value that is within a range from 0 to 1 and that indicates the likeness of a lesion region as the score may be used, or the first training data applied to learning for the first learning model in which the score of a lesion region is set to 1 and the score of a normal mucous membrane region is set to 0 may be used together with the second training data 582. Hereinafter, the second training data 582 having any value within a range from 0 to 1 that indicates the likeness of a lesion region can be referred to as a soft label, and the first training data having the score of a lesion region that is set to 1 and having the score of a normal mucous membrane region that is set to 0 can be referred to as a hard label.

When the hard label is used together with the soft label, the final loss can be calculated by multiplying losses from the respective labels by weights and adding up the loss from the soft label multiplied by the weight and the loss from the hard label multiplied by the weight.

When learning is performed a plurality of times, the weights of the respective losses may be changed in accordance with the number of times learning is performed. A form is preferable in which as the number of times learning is performed increases, the weight of a loss from the hard label is not increased and the weight of a loss from the soft label is not decreased.

In other words, the weight of a loss from the hard label may be decreased from that in the previous learning or may be the same as that in the previous learning. The weight of a loss from the soft label may be increased from that in the previous learning or may be the same as that in the previous learning.

The hard label is suitable for classification of a definite lesion region and a definite normal mucous membrane region. However, the hard label is not good at classification of a lesion region similar to a normal mucous membrane region and a normal mucous membrane region similar to a lesion region.

Therefore, in a stage, such as in the beginning of learning, in which the number of times learning is performed is relatively small, the hard label takes precedence over the soft label, and classification of a definite lesion region and a definite normal mucous membrane region is mainly learned. In a stage in which the learning progresses and learning for classification of a lesion region similar to a normal mucous membrane region and a normal mucous membrane region similar to a lesion region is performed, the soft label takes precedence over the hard label, and classification of a lesion region similar to a normal mucous membrane region and a normal mucous membrane region similar to a lesion region is mainly learned.

The weights for the hard label and the soft label are changed, for example, in a form as described below. In the initial learning, the weight for the hard label is set to 0.9 and the weight for the soft label is set to 0.1. The weight for the hard label is decreased in stages and the weight for the soft label is increased in stages, and in the last learning, the weight for the hard label is set to 0.1 and the weight for the soft label is set to 0.9.

Note that the normal mucous membrane region described in the embodiment is an example of normality data and a normality pixel. The lesion region described in the embodiment is an example of abnormality data and an abnormality pixel.

Figure 5:
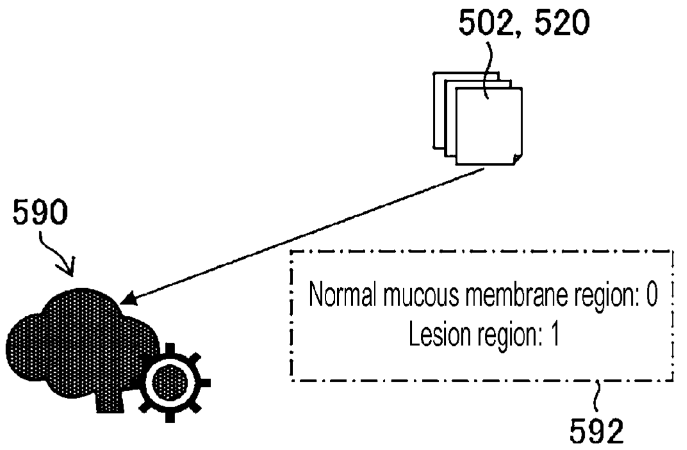
FIG. 5 is a conceptual diagram of a learning model according to a comparative example.

FIG. 5 is a conceptual diagram of a learning model according to a comparative example. To a learning model 590 according to the comparative example, a set of the normal mucous membrane image 502 illustrated in FIG. 1 and training data 592 for the normal mucous membrane image 502 and a set of the lesion image 520 illustrated in FIG. 2 and the training data 592 for the lesion image 520 are applied as a learning data set.

To the training data 592, 0 is applied as a score corresponding to the normal mucous membrane image 502, 1 is applied as a score corresponding to the lesion region in the lesion image 520, and 0 is applied as a score corresponding to a normal mucous membrane region in the lesion image 520. It is difficult to prepare a number of lesion images 520 necessary for learning to be performed for the learning model 590 according to the comparative example, and it is difficult to generate the learning model 590 that is highly accurate.

Figure 6:
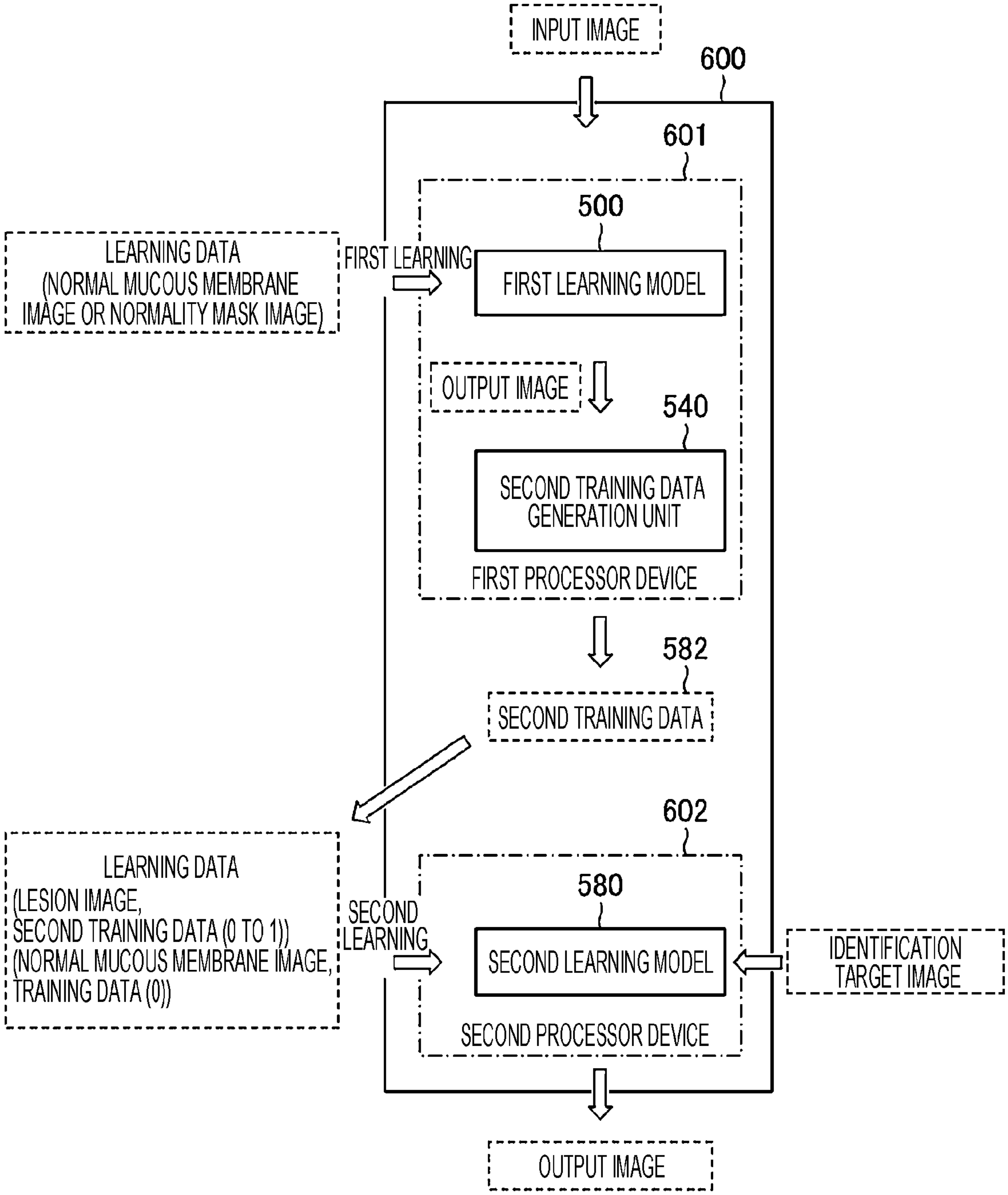
FIG. 6 is a functional block diagram of a learning apparatus according to a first embodiment.

FIG. 6 is a functional block diagram of the learning apparatus according to the first embodiment. The learning apparatus 600 illustrated in FIG. 6 includes the first learning model 500, the second training data generation unit 540, and the second learning model 580. To the hardware of the first learning model 500 and the second training data generation unit 540, a first processor device 601 is applied. For the first learning model 500, the first learning using the normal mucous membrane image 502 or the normality mask image 504 illustrated in FIG. 1 as learning data is performed.

To the hardware of the second learning model 580, a second processor device 602 is applied. For the second learning model 580, the second learning using a set of the lesion image 520 illustrated FIG. 2 and the second training data 582 and a set of the normal mucous membrane image 502 illustrated in FIG. 1 and training data corresponding to the normal mucous membrane image as learning data is performed.

The first processor device 601 may be constituted by a processor device corresponding to the first learning model 500 and a processor device corresponding to the second training data generation unit 540. The first processor device 601, the second training data generation unit 540, and the second processor device 602 may be constituted by a single processor device.

To the second learning model 580, a CNN can be applied. Example configurations of the CNN include an example that includes an input layer, one or more convolutional layers, one or more pooling layers, an affine layer, and an output layer. To the second learning model 580, an image identification model other than a CNN may be applied.

The learning apparatus 600 can be installed in an image processing apparatus that performs, in response to input of the lesion image 520 illustrated in FIG. 2, segmentation of the lesion region 521 in the lesion image 520. Only the second learning model 580, in the learning apparatus 600, that has been trained may be installed in the image processing apparatus. Note that the first processor device 601 and the second processor device 602 described in the embodiment are an example of at least one processor.

Hardware Configuration of Learning Apparatus

To various processing units illustrated in FIG. 6, various processor devices can be applied. The various processor devices include a CPU (Central Processing Unit), a PLD (Programmable Logic Device), and an ASIC (Application-Specific Integrated Circuit).

A CPU is a general-purpose processor device that executes a program to function as the various processing units. A PLD is a processor device having a circuit configuration that is reconfigurable after manufacture. Examples of a PLD include an FPGA (Field-Programmable Gate Array). An ASIC is a dedicated electric circuit having a circuit configuration designed specifically for performing specific processing.

One processing unit may be configured as one of the processor devices described above or two or more processor devices of the same type or different types. For example, one processing unit may be configured as, for example, a plurality of FPGAs. One processing unit may be configured as a combination of one or more FPGAs and one or more CPUs.

One processor device may be used to configure a plurality of processing units. As an example of a configuration in which one processor device is used to configure a plurality of processing units, a form is possible in which one or more CPUs and software are combined to configure one processor device, and the one processor device functions as the plurality of processing units. This form is represented by computers, such as a client terminal device and a server apparatus.

As another example of the configuration, a form is possible in which a processor device is used in which a single IC chip is used to implement the functions of the entire system including a plurality of processing units. This form is represented by, for example, a System-on-Chip. Note that IC is an acronym for Integrated Circuit. A System-on-Chip may be expressed as SoC, which is an acronym for System-on-Chip.

As described above, regarding the hardware configuration, the various processing units are configured by using one or more of the various processor devices described above. Further, the hardware configuration of the various processor devices is more specifically an electric circuit (circuitry) that is a combination of circuit elements, such as semiconductor elements.

Learning Method According to First Embodiment

Figure 7:
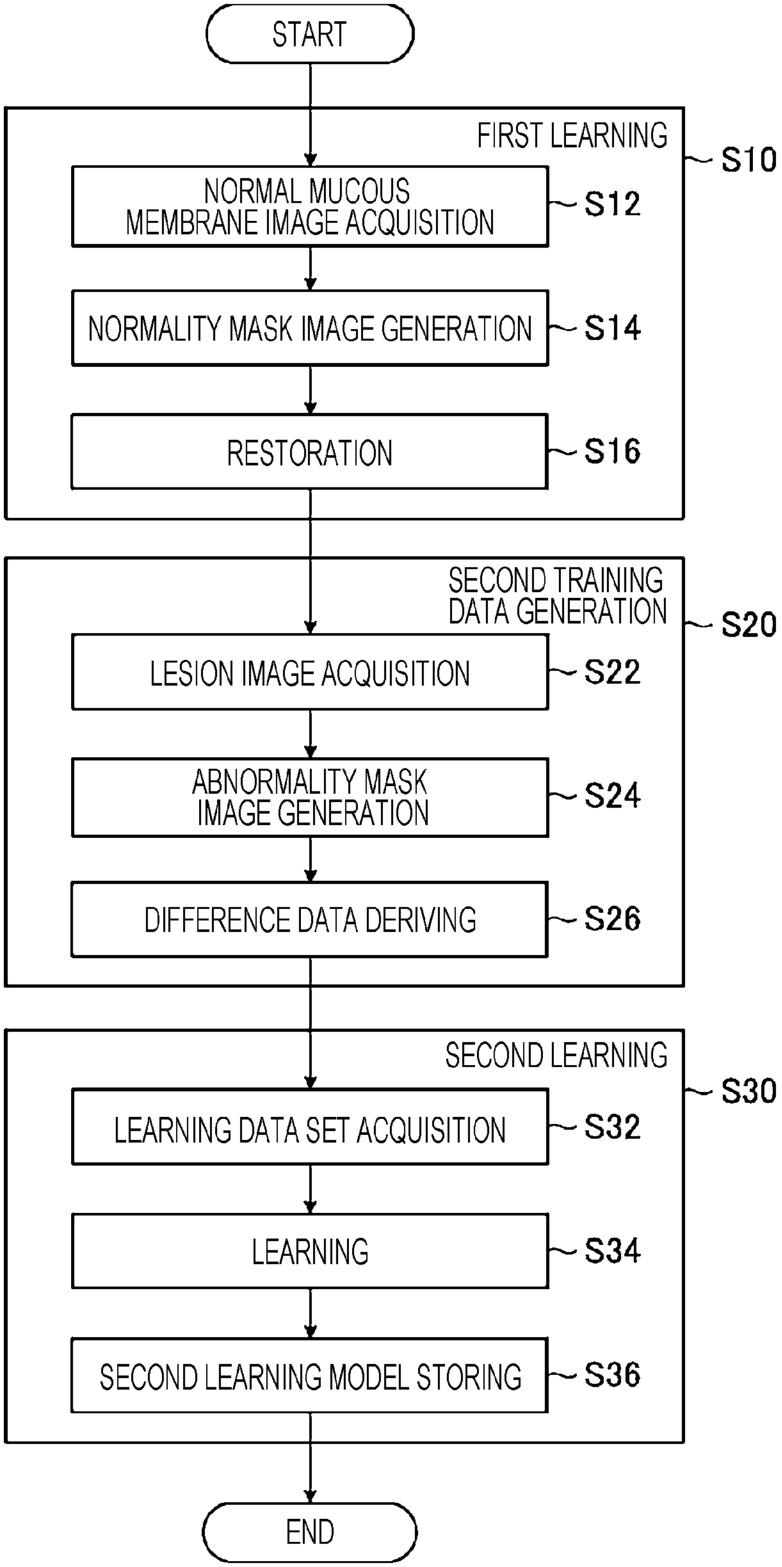
FIG. 7 is a flowchart illustrating a procedure of a learning method according to the first embodiment.

FIG. 7 is a flowchart illustrating a procedure of a learning method according to the first embodiment. The learning method according to the first embodiment includes a first learning step S10, a second training data generation step S20, and a second learning step S30.

To the first learning step S10, the first learning model 500 illustrated in FIG. 1 is applied. The first learning step S10 includes a normal mucous membrane image acquisition step S12, a normality mask image generation step S14, and a restoration step S16. A form can be employed in which the first learning step S10 includes a normality mask image acquisition step instead of the normal mucous membrane image acquisition step S12 and the normality mask image generation step S14.

To the second training data generation step S20, the first learning model 500, illustrated in FIG. 2, that has been trained and the second training data generation unit 540 illustrated in FIG. 6 are applied. The second training data generation step S20 includes a lesion image acquisition step S22, an abnormality mask image generation step S24, and a difference data deriving step S26.

The difference data deriving step S26 can include a normalization processing step. A form can be employed in which the second training data generation step S20 includes an abnormality mask image acquisition step instead of the lesion image acquisition step S22 and the abnormality mask image generation step S24.

To the second learning step S30, the second learning model 580 illustrated in FIG. 6 is applied. The second learning step S30 includes a learning data set acquisition step S32, a supervised learning step S34, and a second learning model storing step S36.

A learning data set acquired in the learning data set acquisition step S32 includes a set of the normal mucous membrane image 502 and training data corresponding to the normal mucous membrane image 502 and a set of the lesion image 520 and the second training data 582 corresponding to the lesion image 520.

In the supervised learning step S34, supervised learning is performed by using the learning data set acquired in the learning data set acquisition step S32. In the second learning model storing step S36, the second learning model 580 that has performed the second learning is stored. The second learning model 580 that has performed the second learning is installed in an image processing apparatus that identifies a lesion region from an endoscopic image.

Effects of First Embodiment

The learning apparatus and the learning method according to the first embodiment can attain the following effects.

[1]

On the basis of an output from the first learning model 500 for which the first learning is performed by using only the normal mucous membrane image 502, the second training data 582 that is applied to the second learning for the second learning model 580 is generated. Accordingly, the second training data 582 applied to the second learning for the second learning model 580 can be generated by using only normal mucous membrane images that can be acquired more easily than lesion images, without preparation of a large number of lesion images.

[2]

For the first learning model 500, learning for compensating for the mask regions 506 in the normality mask image 504 generated from the normal mucous membrane image 502 is performed. Accordingly, the first learning model 500 can compensate for a lost part of an input image.

[3]

The first learning model 500 reduces the dimension of the normal mucous membrane image 502. Accordingly, the first learning model 500 can perform an efficient process at a high speed with a reduced processing load.

[4]

The first learning model 500 makes the size of the restoration image 508 that is output the same as the size of the normal mucous membrane image 502 that is input. Accordingly, when the pseudo normal mucous membrane image 526 output from the first learning model 500 is used to generate the second training data 582, a process for size conversion and so on is not necessary.

[5]

To the first learning model 500, a GAN is applied. Accordingly, the first learning to which unsupervised learning using only the normal mucous membrane image 502 is applied can be performed.

[6]

The second training data generation unit 540 generates the second training data 582 on the basis of the difference data 550 that is the difference between the lesion image 520 and the pseudo normal mucous membrane image 526 output from the first learning model 500 in response to input of the lesion image 520 to the first learning model 500. Accordingly, the second training data 582 corresponding to the lesion image 520 can be generated by using the first learning model 500 for which the first learning using only the normal mucous membrane image 502 has been performed and that has been trained.

Example Configuration of Learning Apparatus According to Second Embodiment

Example of First Learning

Figure 8:
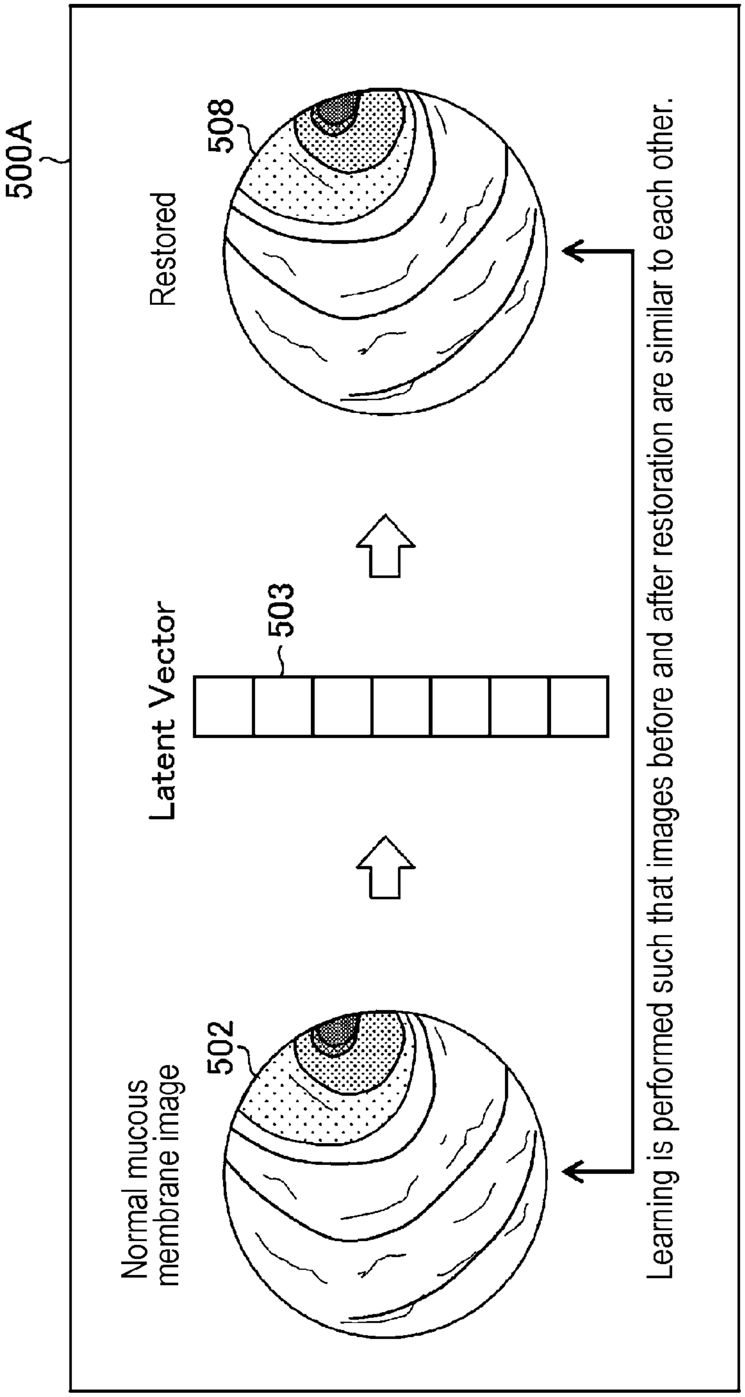
FIG. 8 is a schematic diagram of a first learning model applied to a learning apparatus according to a second embodiment.

FIG. 8 is a schematic diagram of a first learning model applied to a learning apparatus according to a second embodiment. To a first learning model 500A illustrated in FIG. 8, an autoencoder is applied. The autoencoder includes an encoder and a decoder. Note that the encoder and the decoder are not illustrated.

The encoder reduces the normal mucous membrane image 502 to a latent vector 503 by reducing the dimension. The arrow extending from the normal mucous membrane image 502 toward the latent vector 503 illustrated in FIG. 8 indicates the processing by the encoder. For example, the encoder reduces the normal mucous membrane image 502 having a size of 256 pixels×256 pixels to the latent vector 503 of ten dimensions.

The decoder restores from the latent vector 503, the restoration image 508 having a size the same as the size of the normal mucous membrane image 502. The arrow extending from the latent vector 503 to the restoration image 508 indicates the processing by the decoder. To the loss function, the cross-entropy or the L2 loss can be applied. The loss function may be a combination of the cross-entropy and the L2 loss.

Example of Generation of Second Training Data

Figure 9:
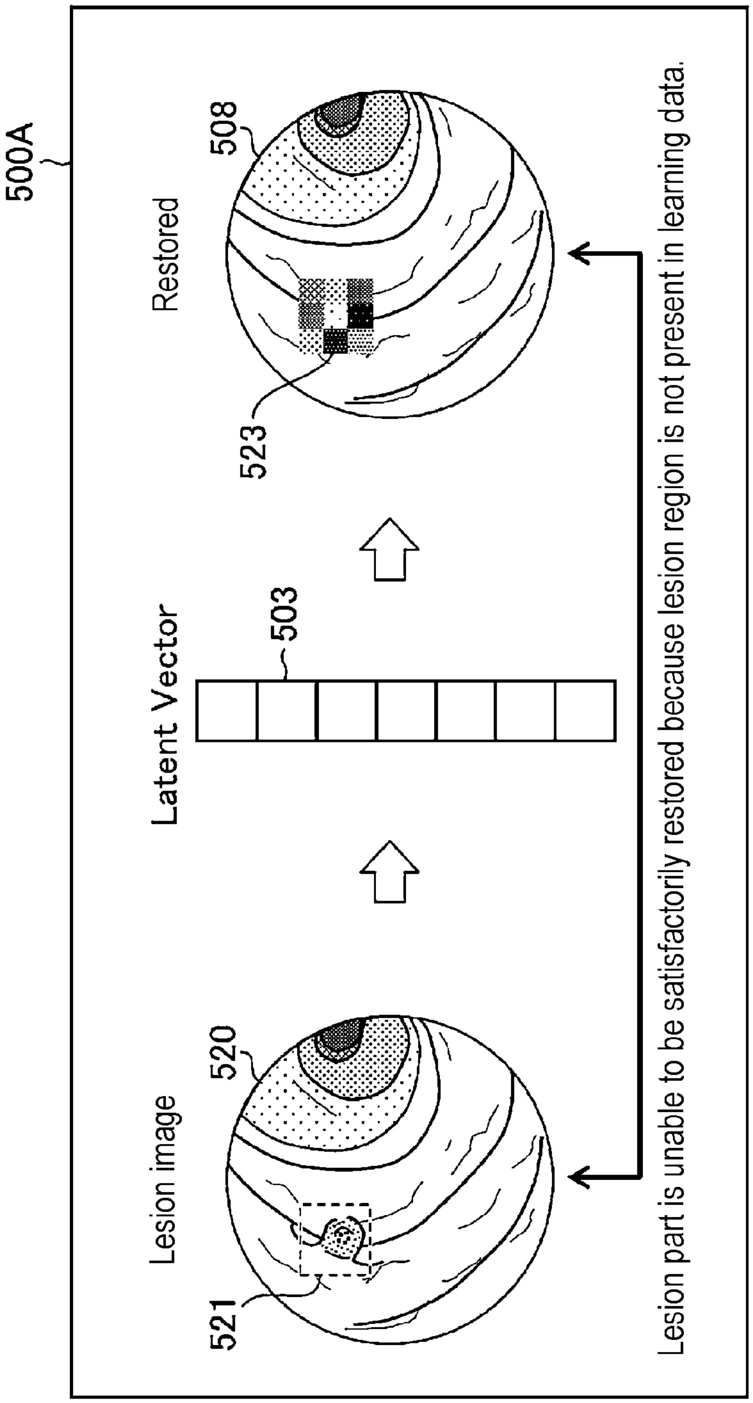
FIG. 9 is a schematic diagram of generation of second training data in the learning apparatus according to the second embodiment.

FIG. 9 is a schematic diagram of generation of second training data in the learning apparatus according to the second embodiment. A frame image that includes a lesion region is extracted from a moving image captured by using an endoscope and the lesion image 520 is prepared. The lesion image 520 is input to the first learning model 500A that has been trained. The first learning model 500A to which the autoencoder is applied has learned only the normal mucous membrane image 502, and therefore, when reducing the dimension to the dimension of the latent vector 503 and restoring the dimension to the original dimension, is unable to satisfactorily restore the lesion region 521 in the lesion image 520. Then, the restoration image 508 having a lesion-corresponding region 523 that corresponds to the lesion region 521 is restored.

Difference data that is the difference between the lesion image 520 and the restoration image 508 is derived. When the lesion region 521 is similar to a normal mucous membrane, the difference data is relatively small. On the other hand, when the lesion region 521 is dissimilar to a normal mucous membrane and is significantly different from a normal mucous membrane, the difference data is relatively large. The difference data may be normalized as in the first learning model 500 according to the first embodiment.

The first learning model 500A that has been trained outputs an output image having a size the same as the size of an input image. When the difference data that is the difference between the lesion image 520 and the restoration image 508 is derived, a size conversion process for the restoration image 508 that is an output image is not necessary.

As in the learning apparatus according to the first embodiment, the difference data generated by applying the first learning model 500A is the second training data 582 applied to the second learning model 580, and can be applied to the second training data 582 corresponding to the lesion image 520. The first learning model 500A that has been trained is installed in the learning apparatus 600 illustrated in FIG. 6.

Effects of Second Embodiment

The learning apparatus and the learning method according to the second embodiment can attain the following effects.

[1]

To the first learning model 500A, the autoencoder is applied. Accordingly, the first learning for restoring the normal mucous membrane image 502 is performed by using only the normal mucous membrane image 502, and the first learning model 500A that has been trained can be generated.

[2]

The second training data 582 applied to the second learning for the second learning model 580 can be generated by using an output image output in response to input of the lesion image 520 to the first learning model 500A that has been trained.

[3]

The second learning for the second learning model 580 is performed by applying a set of the lesion image 520 and the second training data 582 corresponding to the lesion image 520 and a set of the normal mucous membrane image 502 and training data corresponding to the normal mucous membrane image 502. Accordingly, the second learning model 580 that has been trained can be applied to an image processing apparatus that identifies a lesion region from an identification target image.

Example Configuration of Learning Apparatus According to Third Embodiment

In a first learning model applied to a learning apparatus according to a third embodiment, a normal mucous membrane image that includes only a normal mucous membrane and a lesion image that includes a lesion are used as learning data. A large number of normal mucous membrane images and a large number of lesion images are extracted from moving images captured by using an endoscope and prepared. For each of the lesion images, a mask image in which a lesion region is masked is generated.

Figure 13:
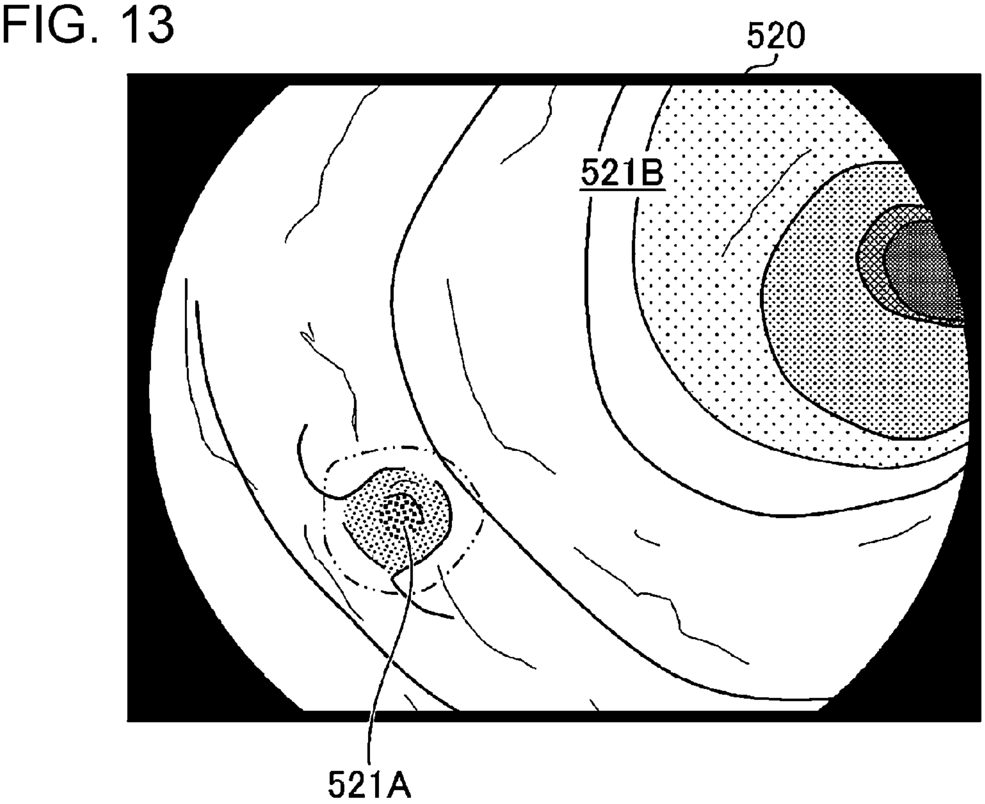
FIG. 13 is a diagram illustrating an example lesion image.

FIG. 13 is a diagram illustrating an example lesion image. FIG. 13 is an enlarged view of the lesion image 520 illustrated in FIG. 2. The lesion image 520 illustrated in FIG. 13 has a lesion region 521A and a normal mucous membrane region 521B.

Figure 14:
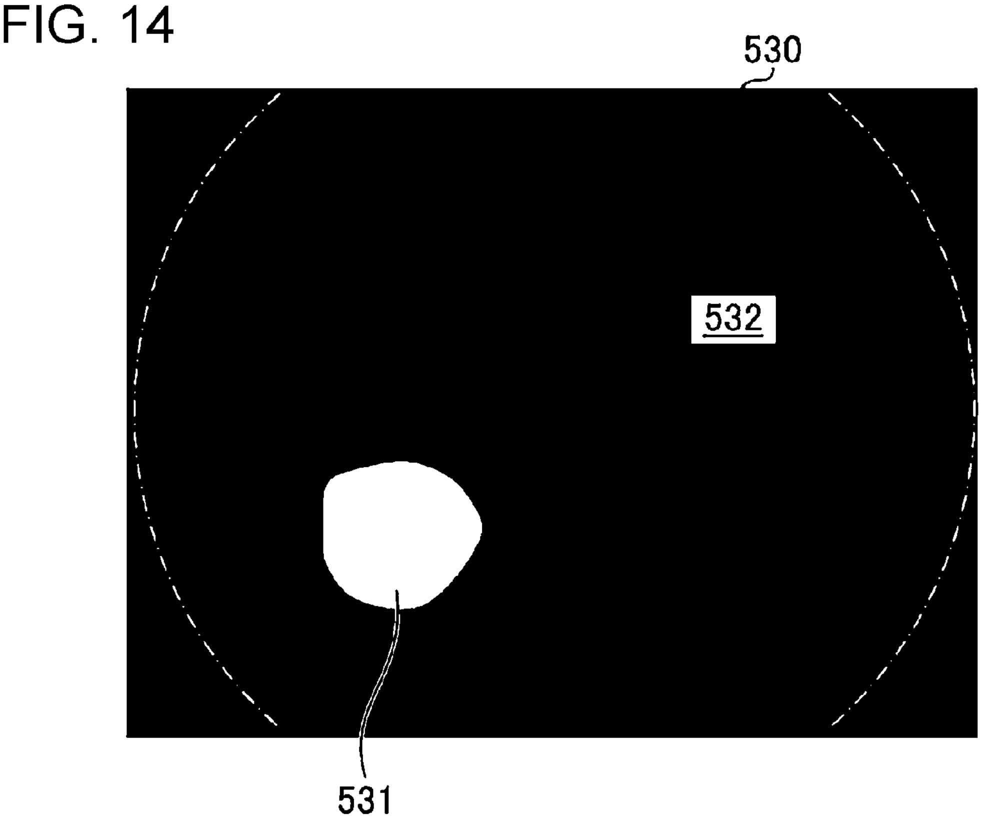
FIG. 14 is a schematic diagram of a mask image corresponding to the lesion image illustrated in FIG. 13.

FIG. 14 is a schematic diagram of a mask image corresponding to the lesion image illustrated in FIG. 13. A mask image 530 illustrated in FIG. 14 is generated on the basis of the lesion image 520 illustrated in FIG. 13 and is a binary image in which the pixel values of the pixels of a mask region 531 corresponding to the lesion region 521A are set to 1 and the pixel values of the pixels of a non-mask region 532 corresponding to the normal mucous membrane region 521B is set to 0. Although FIG. 14 illustrates the mask region 531 having a shape acquired by closely tracing the shape of the lesion, the mask region 531 may be, for example, a circle that circumscribes the lesion or a quadrangle that circumscribes the lesion or may have any shape.

The first learning model is trained by using discrete training values indicated by the normal mucous membrane region 521B and the lesion region 521A so as to output continuous values that indicate the likeness of a lesion region. For example, the entire region of the normal mucous membrane image 502 is assigned 0 as the score, the lesion region 521A in the lesion image 520 is assigned 1 as the score, and the normal mucous membrane region 521B in the lesion image 520 is assigned 0 as the score. To the loss function, for example, the cross-entropy, the hinge loss, or the L2 loss can be applied. To the loss function, a combination of these can be applied.

The abnormality mask image 524 illustrated in FIG. 2 is input to the first learning model that has been trained to acquire an output. The output from the first learning model that has been trained has a value closer to 1 as the mask region 522 is more similar to a lesion or has a value closer to 0 as the mask region 522 is more similar to a normal mucous membrane.

The output from the first learning model that has been trained is used as new training data for the lesion region 521A and a set of the lesion image 520 and the new training data and a set of the normal mucous membrane image 502 and training data are used to perform learning for the second learning model 580 illustrated in FIG. 4.

In the learning for the second learning model 580, only the soft label may be used or the soft label and the hard label may be used together. When the soft label and the hard label are used together, a process similar to that in the second learning model 580 according to the first embodiment can be performed, and a detailed description thereof is omitted here.

Example Application to Other Medical Images

Although example application of the learning apparatus 600 to lesion identification of identifying a lesion region from an endoscopic image has been described in the first embodiment and the second embodiment, the learning apparatus 600 can be applied to lesion identification of identifying a feature region, such as a lesion region, from a medical image other than an endoscopic image, that is, a CT image, an MRI image, or an ultrasound image acquired from a modality other than an endoscope system.

Example Application to Image Processing Apparatus

The learning apparatus 600 according to the first embodiment and the learning apparatus according to the second embodiment can be applied to an image processing apparatus that extracts a feature region from an input image. Examples of the image processing apparatus include an image processing apparatus that detects a crack in a bridge from a captured image acquired by image capturing of the bridge.

Example Application to Signal Processing Apparatus

The learning apparatus 600 according to the first embodiment and the learning apparatus according to the second embodiment can be applied not only to image processing apparatuses. The learning apparatus 600 according to the first embodiment and the learning apparatus according to the second embodiment can be applied also to a signal processing apparatus that processes signals other than images. Note that the meaning of an image can include the meaning of an image signal that indicates an image.

Example Configuration of Endoscope System to which Learning Apparatus is Applied

Overall Configuration of Endoscope System

Figure 10:
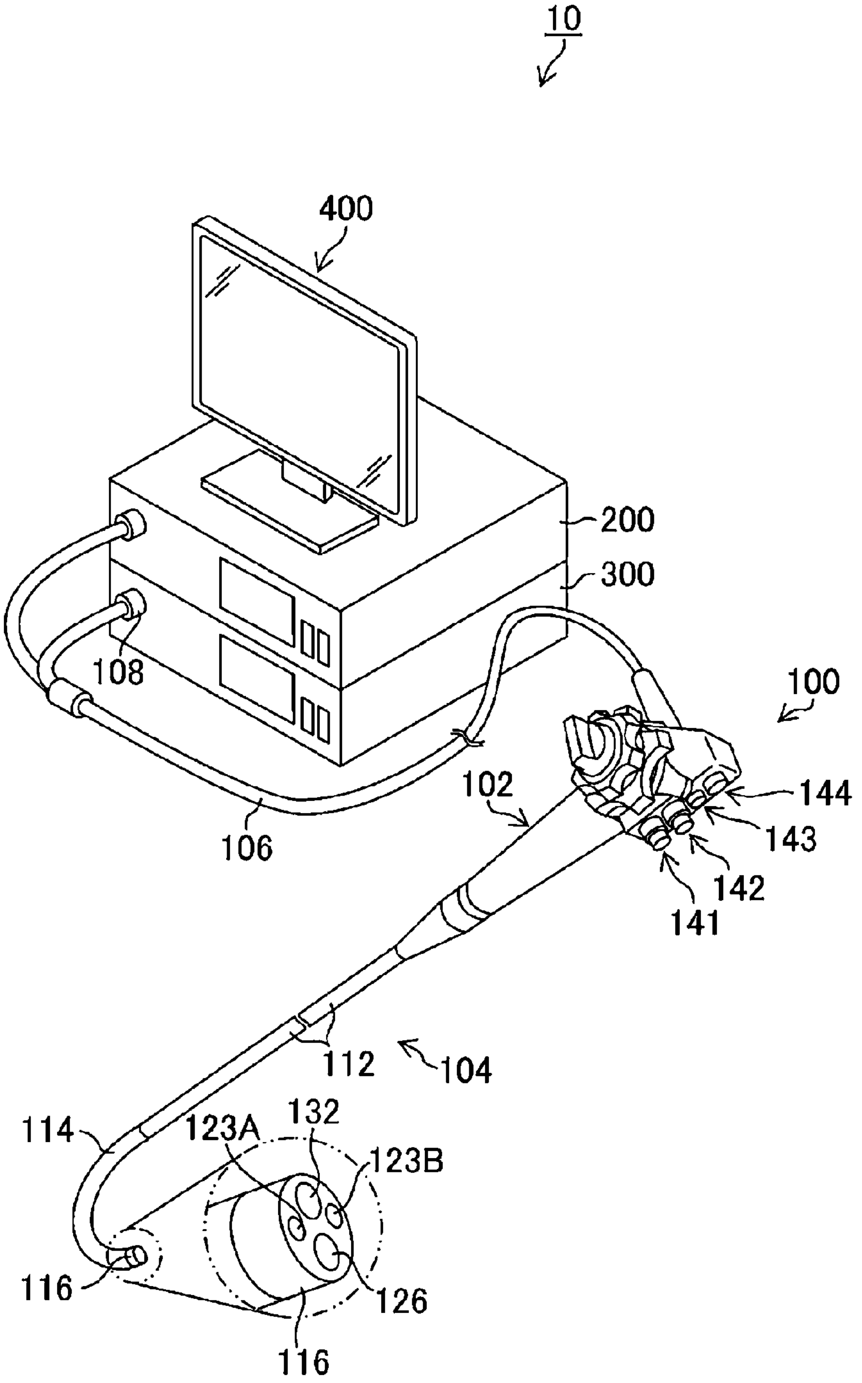
FIG. 10 is a diagram illustrating an overall configuration of an endoscope system.

FIG. 10 is a diagram illustrating an overall configuration of an endoscope system. An endoscope system 10 includes an endoscope main body 100, a processor device 200, a light source device 300, and a display device 400. Note that in FIG. 10, a part of a tip rigid part 116 included in the endoscope main body 100 is enlarged and illustrated.

Example Configuration of Endoscope Main Body

The endoscope main body 100 includes a hand operation part 102 and an insertion part 104. A user holds and operates the hand operation part 102 to insert the insertion part 104 into the body of a subject and observe the inside of the body of the subject. Note that the user is synonymous with, for example, "doctor" and "operator". The subject described here is synonymous with "patient" and "person to be tested".

The hand operation part 102 includes an air/water supply button 141, a suction button 142, a function button 143, and an image capture button 144. The air/water supply button 141 accepts an operation for an air supply instruction and a water supply instruction.

The suction button 142 accepts a suction instruction. The function button 143 is assigned various functions. The function button 143 accepts an instruction for various functions. The image capture button 144 accepts an instruction operation for image capturing. The image capturing includes a moving-image capturing and a still-image capturing.

The insertion part 104 includes a soft part 112, a bending part 114, and the tip rigid part 116. The soft part 112, the bending part 114, and the tip rigid part 116 are disposed in the order of the soft part 112, the bending part 114, and the tip rigid part 116 from the side of the hand operation part 102. That is, the bending part 114 is connected to the proximal end side of the tip rigid part 116, the soft part 112 is connected to the proximal end side of the bending part 114, and the hand operation part 102 is connected to the proximal end side of the insertion part 104.

The user operates the hand operation part 102 to bend the bending part 114 and turn the tip rigid part 116 up, down, right, and left. The tip rigid part 116 includes an image capturing unit, an illumination unit, and a forceps port 126.

FIG. 10 illustrates an image capturing lens 132 that constitutes the image capturing unit. FIG. 10 also illustrates an illumination lens 123A and an illumination lens 123B that constitute the illumination unit. The image capturing unit is assigned a reference numeral 130 and illustrated in FIG. 11. The illumination unit is assigned a reference numeral 123 and illustrated in FIG. 11.

Figure 11:
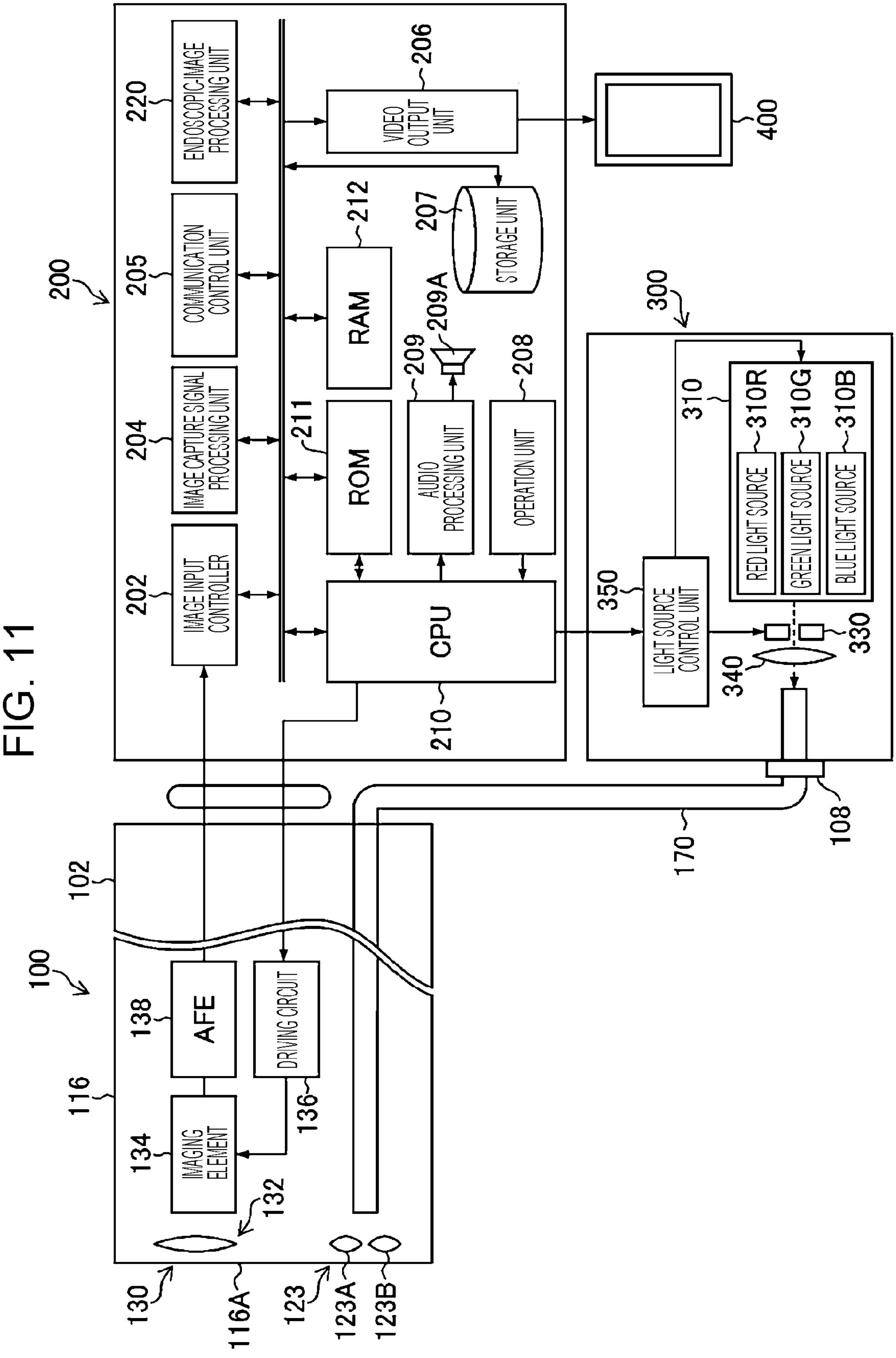
FIG. 11 is a functional block diagram of the endoscope system illustrated in FIG. 10.

During observation and treatment, in response to an operation of an operation unit 208 illustrated in FIG. 11, at least any of white light or narrow-band light is output through the illumination lens 123A and the illumination lens 123B.

When the air/water supply button 141 is operated, wash water is discharged through a water supply nozzle or air is discharged through an air supply nozzle. The wash water and air are used to wash the illumination lens 123A and so on. Note that the water supply nozzle and the air supply nozzle are not illustrated. The water supply nozzle and the air supply nozzle may be provided as a common nozzle.

The forceps port 126 communicates with a pipe line. Into the pipe line, a treatment tool is inserted. The treatment tool is supported as appropriate so as to be able to move forward and backward. When, for example, a tumor or the like is removed, the treatment tool is used to perform necessary treatment. In FIG. 10, a universal cable is assigned a reference numeral 106 and illustrated. A light guide connector is assigned a reference numeral 108 and illustrated.

FIG. 11 is a functional block diagram of the endoscope system. The endoscope main body 100 includes the image capturing unit 130. The image capturing unit 130 is disposed inside the tip rigid part 116. The image capturing unit 130 includes the image capturing lens 132, an imaging element 134, a driving circuit 136, and an analog front end 138. Note that AFE illustrated in FIG. 11 is an acronym for Analog Front End.

The image capturing lens 132 is disposed on a distal-end-side end surface 116A of the tip rigid part 116. At a position on a side of the image capturing lens 132 opposite to the distal-end-side end surface 116A, the imaging element 134 is disposed. To the imaging element 134, a CMOS image sensor is applied. To the imaging element 134, a CCD image sensor may be applied. Note that CMOS is an acronym for Complementary Metal-Oxide Semiconductor. CCD is an acronym for Charge-Coupled Device.

To the imaging element 134, a color imaging element is applied. Examples of the color imaging element include an imaging element that includes RGB color filters. Note that RGB is an acronym for red, green, and blue.

To the imaging element 134, a monochrome imaging element may be applied. When a monochrome imaging element is applied to the imaging element 134, the image capturing unit 130 can perform frame-sequential or color-sequential image capturing while switching the wavelength range of incidence rays incident on the imaging element 134.

The driving circuit 136 supplies to the imaging element 134 various timing signals necessary for operating the imaging element 134 on the basis of a control signal transmitted from the processor device 200.

The analog front end 138 includes an amplifier, a filter, and an AD converter. Note that AD is an acronym for analog and digital. The analog front end 138 performs processes including amplification, noise removal, and analog-digital conversion for an output signal from the imaging element 134. An output signal from the analog front end 138 is transmitted to the processor device 200. Note that AFE illustrated in FIG. 11 is an acronym for Analog Front End.

An optical image of an observation target is formed on a light receiving surface of the imaging element 134 through the image capturing lens 132. The imaging element 134 converts the optical image of the observation target to an electric signal. The electric signal output from the imaging element 134 is transmitted to the processor device 200 through a signal line.

The illumination unit 123 is disposed in the tip rigid part 116. The illumination unit 123 includes the illumination lens 123A and the illumination lens 123B. The illumination lens 123A and the illumination lens 123B are disposed on the distal-end-side end surface 116A at a position adjacent to the image capturing lens 132.

The illumination unit 123 includes a light guide 170. The outgoing end of the light guide 170 is disposed at a position on a side of the illumination lens 123A and the illumination lens 123B opposite to the distal-end-side end surface 116A.

The light guide 170 is inserted into the insertion part 104, the hand operation part 102, and the universal cable 106 illustrated in FIG. 10. The incoming end of the light guide 170 is disposed inside the light guide connector 108.

Example Configuration of Processor Device

The processor device 200 includes an image input controller 202, an image capture signal processing unit 204, and a video output unit 206. The image input controller 202 acquires an electric signal corresponding to an optical image of an observation target and transmitted from the endoscope main body 100.

The image capture signal processing unit 204 generates an endoscopic image of the observation target on the basis of an image capture signal that is the electric signal corresponding to the optical image of the observation target. The endoscopic image is assigned a reference numeral 38 and illustrated in FIG. 12.

To the image capture signal, the image capture signal processing unit 204 can make an image quality correction to which digital signal processing including a white balance process and a shading correction process is applied. The image capture signal processing unit 204 may add accessory information defined by the DICOM standard to the endoscopic image. Note that DICOM is an acronym for Digital Imaging and Communications in Medicine.

The video output unit 206 transmits a display signal indicating the image generated by the image capture signal processing unit 204 to the display device 400. The display device 400 displays the image of the observation target.

When the image capture button 144 illustrated in FIG. 10 is operated, the processor device 200 operates the image input controller 202, the image capture signal processing unit 204, and so on in accordance with an image capture command signal transmitted from the endoscope main body 100.

When acquiring a freeze command signal that indicates still-image capturing from the endoscope main body 100, the processor device 200 uses the image capture signal processing unit 204 to generate a still image based on a frame image at the timing when the image capture button 144 is operated. The processor device 200 uses the display device 400 to display the still image. The frame image is assigned a reference numeral 38B and illustrated in FIG. 12. The still image is assigned a reference numeral 39 and illustrated in FIG. 12.

The processor device 200 includes a communication control unit 205. The communication control unit 205 controls communication with an apparatus that is connected via an intra-hospital system, an intra-hospital LAN, and so on so as to be able to communicate. To the communication control unit 205, a communication protocol conforming to the DICOM standard can be applied. Examples of the intra-hospital system include an HIS (Hospital Information System). LAN is an acronym for Local Area Network.

The processor device 200 includes a storage unit 207. The storage unit 207 stores an endoscopic image generated by using the endoscope main body 100. The storage unit 207 may store various types of information attached to the endoscopic image.

The processor device 200 includes the operation unit 208. The operation unit 208 outputs a command signal corresponding to a user operation. To the operation unit 208, a keyboard, a mouse, a joystick, and so on can be applied.

The processor device 200 includes an audio processing unit 209 and a speaker 209A. The audio processing unit 209 generates an audio signal that indicates information to be provided as sound. The speaker 209A converts the audio signal generated by the audio processing unit 209 to sound. Examples of the sound output from the speaker 209A include a message, audio guidance, and an alarm.

The processor device 200 includes a CPU 210, a ROM 211, and a RAM 212. ROM is an acronym for Read-Only Memory. RAM is an acronym for Random Access Memory.

The CPU 210 functions as an overall control unit of the processor device 200. The CPU 210 functions as a memory controller that controls the ROM 211 and the RAM 212. The ROM 211 stores various programs, control parameters, and so on applied to the processor device 200.

The RAM 212 is used as a temporary storage area for data used in various processes and as a processing area for computational processing by the CPU 210. The RAM 212 can be used as a buffer memory when an endoscopic image is acquired.

The processor device 200 performs various processes for an endoscopic image generated by using the endoscope main body 100 and uses the display device 400 to display the endoscopic image and various types of information attached to the endoscopic image. The processor device 200 stores the endoscopic image and the various types of information attached to the endoscopic image.

That is, during an endoscopy using the endoscope main body 100, the processor device 200 performs display of an endoscopic image and so on using the display device 400, output of audio information using the speaker 209A, and various processes for the endoscopic image.

The processor device 200 includes an endoscopic-image processing unit 220. To the endoscopic-image processing unit 220, the learning apparatus 600 illustrated in FIG. 6 is applied. The endoscopic-image processing unit 220 identifies a lesion region from an endoscopic image.

Hardware Configuration of Processor Device

To the processor device 200, a computer can be applied. To the computer, hardware described below is applied, and the functions of the processor device 200 can be implemented by executing a specified program. Note that the program is synonymous with "software".

To the processor device 200, various processors can be applied as a signal processing unit that performs signal processing. Examples of the processors include a CPU and a GPU (Graphics Processing Unit). A CPU is a general-purpose processor that functions as a signal processing unit by executing a program. A GPU is a processor specialized in image processing. To the hardware of the processors, an electric circuit that is a combination of electric circuit elements, such as semiconductor elements, can be applied. Each control unit includes a ROM that stores a program and so on and a RAM that is, for example, a work area for various computations.

To one signal processing unit, two or more processors may be applied. The two or more processors may be processors of the same type or processors of different types. To a plurality of signal processing units, one processor may be applied. The processor device 200 described in the embodiment corresponds to an example of an endoscope control unit.

Example Configuration of Light Source Device

The light source device 300 includes a light source 310, an aperture diaphragm 330, a condensing lens 340, and a light source control unit 350. The light source device 300 causes observation light to incident on the light guide 170.

The light source 310 includes a red light source 310R, a green light source 310G, and a blue light source 310B. The red light source 310R, the green light source 310G, and the blue light source 310B respectively emit a red narrow-band light ray, a green narrow-band light ray, and a blue narrow-band light ray.

The light source 310 can generate illumination light that is a combination of any of the red, green, and, blue narrow-band light rays. For example, the light source 310 can combine the red, green, and blue narrow-band light rays to generate white light. The light source 310 can combine any two color light rays among the red, green, and blue narrow-band light rays to generate narrow-band light.

The light source 310 can use any one color light ray among the red, green, and blue narrow-band light rays to generate narrow-band light. The light source 310 can selectively switch and emit white light or narrow-band light. Note that narrow-band light is synonymous with "special light". The light source 310 can include an infrared light source that emits infrared light and an ultraviolet light source that emits ultraviolet light.

The light source 310 can employ a form that includes a white light source that emits white light, a filter that transmits white light, and a filter that transmits narrow-band light. The light source 310 having such a form can selectively emit any of white light or narrow-band light by switching between the filter that transmits white light and the filter that transmits narrow-band light.

The filter that transmits narrow-band light can include a plurality of filters corresponding to different ranges. The light source 310 can selectively emit a plurality of narrow-band light rays in different ranges by selective switching between the plurality of filters corresponding to different ranges.

To the light source 310, for example, a type and a wavelength range corresponding to the type of observation target, the purpose of observation, and so on can be applied. Examples of the type of the light source 310 include a laser light source, a xenon light source, and an LED light source. Note that LED is an acronym for Light-Emitting Diode.

When the light guide connector 108 is connected to the light source device 300, observation light emitted from the light source 310 reaches the incoming end of the light guide 170 through the aperture diaphragm 330 and the condensing lens 340. The observation light is emitted to an observation target through the light guide 170, the illumination lens 123A, and so on.

The light source control unit 350 transmits a control signal to the light source 310 and the aperture diaphragm 330 on the basis of a command signal transmitted from the processor device 200. The light source control unit 350 controls, for example, the illuminance of observation light emitted from the light source 310, switching of the observation light, and turning on and off of the observation light.

Example Configuration of Endoscopic-Image Processing Unit

Figure 12:
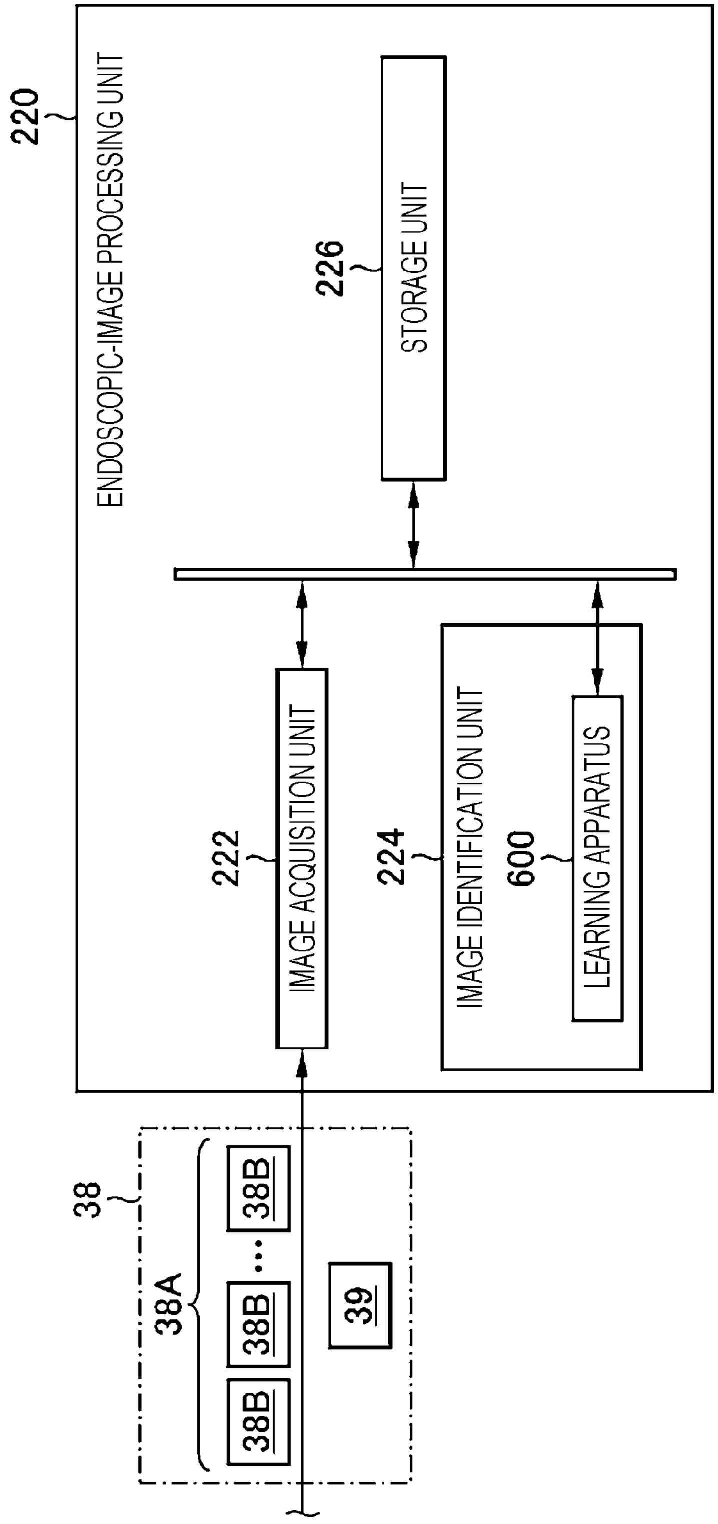
FIG. 12 is a block diagram of an endoscopic-image processing unit illustrated in FIG. 11.

FIG. 12 is a block diagram of the endoscopic-image processing unit illustrated in FIG. 11. The endoscopic-image processing unit 220 illustrated in FIG. 12 includes an image acquisition unit 222, an image identification unit 224, and a storage unit 226.

The image acquisition unit 222 acquires the endoscopic image 38 captured by using the endoscope main body 100 illustrated in FIG. 10. Hereinafter, acquisition of the endoscopic image 38 can include acquisition of a moving image 38A, acquisition of the frame images 38B, and acquisition of the still image 39. The image acquisition unit 222 stores the endoscopic image 38 in the storage unit 226.

The image acquisition unit 222 can acquire the moving image 38A formed of the frame images 38B in time series. The image acquisition unit 222 can acquire the still image 39 when still-image capturing is performed in the middle of capturing of the moving image 38A.

The image identification unit 224 identifies a lesion region from the endoscopic image 38 acquired via the image acquisition unit 222. The image identification unit 224 includes the learning apparatus 600 described with reference to FIG. 1 to FIG. 9.

The image identification unit 224 stores the result of identification of a lesion region in the storage unit 226. Examples of the result of identification of a lesion region include highlighted display of a lesion region in the endoscopic image, such as superimposed display of a bounding box that indicates a lesion region in the endoscopic image.

Modifications of Endoscope System

Modification of Illumination Light

An example of a medical image that can be acquired by using the endoscope system 10 illustrated in FIG. 10 is a normal-light image acquired by emitting light in a white range or by emitting light rays in a plurality of wavelength ranges as light in the white range.

Another example of a medical image that can be acquired by using the endoscope system 10 described in the embodiment is an image acquired by emitting light in a specific wavelength range. To the specific wavelength range, a range narrower than the white range can be applied. The following modifications are applicable.

First Modification

A first example of the specific wavelength range is a blue range or a green range that is a visible range. The wavelength range in the first example includes a wavelength range of 390 nanometers or more and 450 nanometers or less or a wavelength range of 530 nanometers or more and 550 nanometers or less, and light in the first example has a peak wavelength within a wavelength range of 390 nanometers or more and 450 nanometers or less or a wavelength range of 530 nanometers or more and 550 nanometers or less.

Second Modification

A second example of the specific wavelength range is a red range that is a visible range. The wavelength range in the second example includes a wavelength range of 585 nanometers or more and 615 nanometers or less or a wavelength range of 610 nanometers or more and 730 nanometers or less, and light in the second example has a peak wavelength within a wavelength range of 585 nanometers or more and 615 nanometers or less or a wavelength range of 610 nanometers or more and 730 nanometers or less.

Third Modification

A third example of the specific wavelength range includes a wavelength range in which the light absorption coefficient differs between oxyhemoglobin and reduced hemoglobin, and light in the third example has a peak wavelength within a wavelength range in which the light absorption coefficient differs between oxyhemoglobin and reduced hemoglobin. The wavelength range in the third example includes a wavelength range of 400±10 nanometers, a wavelength range of 440±10 nanometers, a wavelength range of 470±10 nanometers, or a wavelength range of 600 nanometers or more and 750 nanometers or less, and light in the third example has a peak wavelength within a wavelength range of 400±10 nanometers, a wavelength range of 440±10 nanometers, a wavelength range of 470±10 nanometers, or a wavelength range of 600 nanometers or more and 750 nanometers or less.

Fourth Modification

A fourth example of the specific wavelength range is a wavelength range used in observation of fluorescence emitted by a fluorescent substance in a living body and is a wavelength range of exciting light that excites the fluorescent substance. The wavelength range is, for example, a wavelength range of 390 nanometers or more and 470 nanometers or less. Observation of fluorescent light may be called fluorescent observation.

Fifth Modification

A fifth example of the specific wavelength range is a wavelength range of infrared light. The wavelength range in the fifth example includes a wavelength range of 790 nanometers or more and 820 nanometers or less or a wavelength range of 905 nanometers or more and 970 nanometers or less, and light in the fifth example has a peak wavelength within a wavelength range of 790 nanometers or more and 820 nanometers or less or a wavelength range of 905 nanometers or more and 970 nanometers or less.

Example Generation of Special-Light Image

The processor device 200 may generate a special-light image having information about the specific wavelength range on the basis of a normal-light image captured by using white light. Generation described here includes acquisition. In this case, the processor device 200 functions as a special-light image acquisition unit. The processor device 200 acquires a signal in the specific wavelength range by performing computation based on color information of red, green, and blue or cyan, magenta, and yellow included in the normal-light image.

Cyan, magenta, and yellow may be expressed as CMY, which is an acronym for cyan, magenta, and yellow.

Example Generation of Feature Value Image

As a medical image, a feature value image can be generated by performing computation based on at least any of a normal-light image acquired by emitting light in the white range or by emitting light rays in a plurality of wavelength ranges as light in the white range or a special-light image acquired by emitting light in the specific wavelength range.

Example Application to Program

The learning apparatus and the learning method described above can be configured as a program that implements functions corresponding to the units of the learning apparatus and the steps of the learning method by using a computer. Examples of the functions implemented by using a computer include a function of generating the first learning model, a function of generating the second training data, and a function of generating the second learning model.

The program that causes a computer to implement the learning functions described above can be stored in a computer-readable information storage medium that is a tangible non-transitory information storage medium and can be provided from the information storage medium.

Instead of the form in which the program is stored in a non-transitory information storage medium and provided, a form can be employed in which a program signal is provided via a communication network.

Combination of Embodiments, Modifications, and so on

The components described in the embodiments described above can be combined as appropriate and used, and some of the components can be replaced.

In the embodiments of the present invention described above, any configuration requirement can be changed, added, or deleted as appropriate without departing from the spirit of the present invention. The present invention is not limited to the above-described embodiments, and various modifications can be made by a person having ordinary skill in the art within the technical ideas of the present invention.

REFERENCE SIGNS LIST

10 endoscope system
38 endoscopic image
38A moving image
38B frame image
39 still image
100 endoscope main body
102 hand operation part
104 insertion part
106 universal cable
108 light guide connector
112 soft part
114 bending part
116 tip rigid part
116A distal-end-side end surface
123 illumination unit
123A illumination lens
123B illumination lens
126 forceps port
130 image capturing unit
132 image capturing lens
134 imaging element
136 driving circuit
138 analog front end
141 air/water supply button
142 suction button
143 function button
144 image capture button
170 light guide
200 processor device
202 image input controller
204 image capture signal processing unit
205 communication control unit
206 video output unit
207 storage unit
208 operation unit
209 audio processing unit
209A speaker
210 CPU
211 ROM
212 RAM
220 endoscopic-image processing unit

222 image acquisition unit
224 image identification unit
226 storage unit
300 light source device
310 light source
310B blue light source
310G green light source
310R red light source
330 aperture diaphragm
340 condensing lens
350 light source control unit
400 display device
500 first learning model
500A first learning model
502 normal mucous membrane image
503 latent vector
504 normality mask image
506 mask region
508 restoration image
520 lesion image
521 lesion region
521A lesion region
521B normal mucous membrane region
522 mask region
523 lesion-corresponding region
524 abnormality mask image
526 pseudo normal mucous membrane image
530 mask image
531 mask region
532 non-mask region
540 second training data generation unit
550 difference data
580 second learning model
582 second training data
583 training data
590 learning model
592 training data
600 learning apparatus
601 first processor device
602 second processor device
S10 to S36 steps of learning method

What is claimed is:

1. A learning apparatus comprising at least one processor, the processor being configured to generate a first learning model by performing first learning using only normality data as learning data or by performing first learning using only normality mask data as learning data, wherein the normality mask data is generated by performing masking on a part of the normality data, generate abnormality mask data that is generated by performing masking on an abnormal part of abnormality data, and generate second training data to be applied to a second learning model that identifies identification target data, by using difference data, wherein the difference data is a difference between the abnormality data input to the first learning model and output data output from the first learning model in response to input of the abnormality mask data to the first learning model.

2. The learning apparatus according to claim 1, wherein the processor is configured to generate the first learning model that outputs, for input data having a masked part, output data in which the masked part is compensated for.

3. The learning apparatus according to claim 1, wherein the processor is configured to generate the first learning model that reduces a dimension of input data and outputs output data for which the reduced dimension is restored.

4. The learning apparatus according to claim 1, wherein the processor is configured to generate the first learning model that outputs output data having a size the same as a size of input data.

5. The learning apparatus according to claim 1, wherein the processor is configured to generate the first learning model to which a generative adversarial network is applied, by performing the first learning using only the normality mask data as learning data.

6. The learning apparatus according to claim 1, wherein the processor is configured to generate the first learning model to which an autoencoder is applied, by performing the first learning using only the normality data as learning data.

7. The learning apparatus according to claim 1, wherein the processor is configured to generate the second training data by performing normalization on the difference data.

8. The learning apparatus according to claim 1, wherein the processor is configured to generate the second learning model by performing second learning using a set of the abnormality data and the second training data as learning data.

9. The learning apparatus according to claim 8, wherein the processor is configured to perform the second learning using a set of the normality data and first training data corresponding to the normality data as learning data.

10. The learning apparatus according to claim 8, wherein the processor is configured to perform the second learning for the second learning model by using as the second training data, a hard label that has discrete training values indicating the normality data and the abnormality data and that is applied to the first learning and a soft label that has continuous training values indicating an abnormality-likeness and that is generated by using output data from the first learning model.

11. The learning apparatus according to claim 10, wherein the processor is configured to perform the second learning a plurality of times, and not increase a weight used for the hard label and not decrease a weight used for the soft label as the number of times the second learning is performed increases.

12. The learning apparatus according to claim 7, wherein the processor is configured to generate the second learning model to which a convolutional neural network is applied.

13. A learning method for causing a computer to generate a first learning model by performing first learning using only normality data as learning data or by performing first learning using only normality mask data as learning data, wherein the normality mask data is generated by performing masking on a part of the normality data, generate abnormality mask data that is generated by performing masking on an abnormal part of abnormality data, and generate second training data to be applied to a second learning model that identifies identification target data, by using difference data, wherein the difference data is a difference between the abnormality data input to the first learning model and output data output from the first learning model in response to input of the abnormality mask data to the first learning model.

14. An image processing apparatus comprising at least one processor, the processor being configured to generate an abnormality mask image that is generated by performing masking on an abnormal part of an abnormality image, generate a second learning model by performing second learning using a set of second training data and the abnormality image as learning data, the second training data being generated by using difference data, wherein the different data is a difference between the abnormality image input to a first learning model and an output image output from the first learning model in response to input of the abnormality mask image to the first learning model, the second training data being applied to the second learning model that identifies presence or absence of an abnormality in an identification target image, the first learning model being generated by performing first learning using only a normality image as learning data or by performing first learning using only a normality mask image as learning data, wherein the normality mask image is generated by performing masking on a part of the normality image, and determine whether an identification target image is a normality image by using the second learning model.

15. The image processing apparatus according to claim 14, wherein the second learning model performs segmentation of an abnormal part for the identification target image.

16. An endoscope system comprising:

an endoscope; and at least one processor, the processor being configured to generate an abnormality mask image by performing masking on an abnormal part of an abnormality image, generate a second learning model by performing second learning using a set of second training data and the abnormality image as learning data, the second training data being generated by using difference data, wherein the different data is a difference between the abnormality image input to a first learning model and an output image output from the first learning model in response to input of the abnormality mask image to the first learning model, the second training data being applied to the second learning model that identifies presence or absence of an abnormality in an identification target image, the first learning model being generated by performing first learning using only a normality image as learning data or by performing first learning using only a normality mask image as learning data, wherein the normality mask image is generated by performing masking on a part of a normality image, and determine presence or absence of an abnormality in an endoscopic image acquired from the endoscope, by using the second learning model.

17. The endoscope system according to claim 16, wherein the processor is configured to perform the second learning by applying the second training data that is generated by using the first learning model for which the first learning is performed by applying an endoscopic image that is a normal mucous membrane image as the normality image, and by applying an endoscopic image that includes a lesion region as the abnormality image.

18. The endoscope system according to claim 17, wherein the processor is configured to perform the second learning by using a set of the second training data and the abnormality image and a set of a normality image and first training data corresponding to the normality image as learning data, and generate the second learning model that performs segmentation of an abnormal part in an identification target image, the second training data corresponding to the abnormality image and generated by normalizing the difference data, the first learning performed for the first learning model being learning for restoring the normal mucous membrane image from a normal mucous membrane mask image generated by performing masking on a part of the normal mucous membrane image and for generating a normality restoration image.

19. A non-transitory, computer-readable tangible recording medium which records thereon, a program for causing, when read by a computer, the computer to implement a function of generating a first learning model by performing first learning using only normality data as learning data or by performing first learning using only normality mask data as learning data, wherein the normality mask data is generated by performing masking on a part of the normality data, a function of generating abnormality mask data by performing masking on an abnormal part of abnormality data, a function of generating second training data to be applied to a second learning model that identifies presence or absence of an abnormality in identification target data, by using difference data, wherein the difference data is a difference between the abnormality data input to the first learning model and output data output from the first learning model in response to input of the abnormality mask data to the first learning model.

* * * * *